United States Patent
Shelton, IV et al.

(10) Patent No.: US 12,357,308 B2
(45) Date of Patent: Jul. 15, 2025

(54) PAN-LESS STAPLE CARTRIDGE ASSEMBLY COMPRISING RETENTION FEATURES FOR HOLDING STAPLE DRIVERS AND SLED

(71) Applicant: Cilag GmbH International, Zug (CH)

(72) Inventors: Frederick E. Shelton, IV, Hillsboro, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/379,803

(22) Filed: Oct. 13, 2023

(65) Prior Publication Data
US 2025/0120713 A1   Apr. 17, 2025

(51) Int. Cl.
*A61B 17/072* (2006.01)

(52) U.S. Cl.
CPC ......... *A61B 17/07207* (2013.01); *A61B 2017/07271* (2013.01); *A61B 2017/07278* (2013.01)

(58) Field of Classification Search
CPC .... A61B 17/07207; A61B 2017/07271; A61B 2017/07278; A61B 2017/07285
USPC .......................... 227/175.1–182.1
See application file for complete search history.

(56) References Cited

U.S. PATENT DOCUMENTS

| | | |
|---|---|---|
| 5,403,312 A | 4/1995 | Yates et al. |
| 6,988,649 B2 | 1/2006 | Shelton, IV et al. |
| 7,000,818 B2 | 2/2006 | Shelton, IV et al. |
| 7,287,682 B1 * | 10/2007 | Ezzat .................. A61B 17/072 227/181.1 |
| 7,401,721 B2 | 7/2008 | Holsten et al. |
| 7,407,075 B2 | 8/2008 | Holsten et al. |
| 7,422,139 B2 | 9/2008 | Shelton, IV et al. |
| 7,464,849 B2 | 12/2008 | Shelton, IV et al. |
| 7,669,746 B2 | 3/2010 | Shelton, IV et al. |
| 7,670,334 B2 | 3/2010 | Hueil et al. |

(Continued)

FOREIGN PATENT DOCUMENTS

| | | |
|---|---|---|
| CN | 105919642 A | 9/2016 |
| CN | 105997172 A | 10/2016 |

(Continued)

OTHER PUBLICATIONS

U.S. Appl. No. 12/031,573, filed Feb. 14, 2008.

(Continued)

*Primary Examiner* — Stephen F. Gerrity
*Assistant Examiner* — Linda J Hodge

(57) ABSTRACT

A staple cartridge assembly for use with a surgical stapling instrument is disclosed. The staple cartridge assembly comprises a plurality of staples, a plurality of staple drivers, and a cartridge body comprising a retention feature. The staple cartridge assembly further comprises a sled movable longitudinally through the cartridge body from a proximal unfired position to a distal fired position during a firing stroke, wherein the sled comprises a ramp configured to lift the staple drivers toward a deck to eject the staples from staple cavities during the firing stroke, wherein the sled comprises a longitudinally-extending slot, wherein the retention feature supports at least one of the staple drivers in an unlifted position, and wherein the longitudinally-extending slot of the sled is configured to receive the retention feature during the firing stroke.

20 Claims, 14 Drawing Sheets

(56) References Cited

U.S. PATENT DOCUMENTS

| | | | |
|---|---|---|---|
| 7,735,703 B2 | 6/2010 | Morgan et al. |
| 7,753,245 B2 | 7/2010 | Boudreaux et al. |
| 7,845,537 B2 | 12/2010 | Shelton, IV et al. |
| 7,980,443 B2 | 7/2011 | Scheib et al. |
| 8,123,100 B2 | 2/2012 | Holsten et al. |
| 8,141,762 B2 | 3/2012 | Bedi et al. |
| 8,210,411 B2 | 7/2012 | Yates et al. |
| 8,220,688 B2 | 7/2012 | Laurent et al. |
| 8,308,040 B2 | 11/2012 | Huang et al. |
| 8,393,514 B2 | 3/2013 | Shelton, IV et al. |
| 8,540,133 B2 | 9/2013 | Bedi et al. |
| 8,561,870 B2 | 10/2013 | Baxter, III et al. |
| 8,608,045 B2 | 12/2013 | Smith et al. |
| 8,733,613 B2 | 5/2014 | Huitema et al. |
| 8,864,007 B2 | 10/2014 | Widenhouse et al. |
| 8,876,857 B2 | 11/2014 | Burbank |
| 9,050,083 B2 | 6/2015 | Yates et al. |
| 9,072,535 B2 | 7/2015 | Shelton, IV et al. |
| 9,101,358 B2 | 8/2015 | Kerr et al. |
| 9,131,940 B2 | 9/2015 | Huitema et al. |
| 9,211,120 B2 * | 12/2015 | Scheib ............... A61B 17/068 |
| 9,345,481 B2 | 5/2016 | Hall et al. |
| 9,629,631 B2 | 4/2017 | Nicholas et al. |
| 9,770,245 B2 | 9/2017 | Swayze et al. |
| 9,788,835 B2 | 10/2017 | Morgan et al. |
| 9,924,944 B2 | 3/2018 | Shelton, IV et al. |
| 9,987,008 B2 | 6/2018 | Scirica et al. |
| 10,080,552 B2 | 9/2018 | Nicholas et al. |
| 10,085,749 B2 | 10/2018 | Cappola et al. |
| 10,105,142 B2 | 10/2018 | Baxter, III et al. |
| 10,123,798 B2 | 11/2018 | Baxter, III et al. |
| 10,130,363 B2 | 11/2018 | Huitema et al. |
| 10,166,023 B2 | 1/2019 | Vendely et al. |
| 10,213,203 B2 | 2/2019 | Swayze et al. |
| 10,299,792 B2 | 5/2019 | Huitema et al. |
| 10,357,252 B2 | 7/2019 | Harris et al. |
| 10,517,599 B2 | 12/2019 | Baxter, III et al. |
| 10,537,324 B2 | 1/2020 | Shelton, IV et al. |
| 10,542,981 B2 | 1/2020 | Miller et al. |
| 10,561,419 B2 | 2/2020 | Beardsley |
| 10,568,624 B2 | 2/2020 | Shelton, IV et al. |
| 10,765,427 B2 | 9/2020 | Shelton, IV et al. |
| 10,898,191 B2 | 1/2021 | Huitema et al. |
| 10,945,727 B2 | 3/2021 | Shelton, IV et al. |
| 10,952,724 B2 | 3/2021 | Shelton, IV et al. |
| 11,000,278 B2 | 5/2021 | Shelton, IV et al. |
| 11,045,191 B2 | 6/2021 | Shelton, IV et al. |
| 11,058,426 B2 | 7/2021 | Nalagatla et al. |
| D933,220 S | 10/2021 | Tate et al. |
| 11,147,552 B2 | 10/2021 | Burbank et al. |
| 11,207,065 B2 | 12/2021 | Harris et al. |
| 11,229,433 B2 | 1/2022 | Schings et al. |
| 11,234,698 B2 | 2/2022 | Shelton, IV et al. |
| 11,234,700 B2 | 2/2022 | Ragosta et al. |
| 11,291,445 B2 | 4/2022 | Shelton, IV et al. |
| 11,337,693 B2 | 5/2022 | Hess et al. |
| 11,382,625 B2 | 7/2022 | Huitema et al. |
| 11,382,627 B2 | 7/2022 | Huitema et al. |
| D967,421 S | 10/2022 | Shelton, IV et al. |
| 11,490,890 B2 | 11/2022 | Harris et al. |
| 11,517,315 B2 | 12/2022 | Huitema et al. |
| D974,560 S | 1/2023 | Shelton, IV et al. |
| 11,540,826 B2 | 1/2023 | Nalagatla et al. |
| 11,571,213 B2 | 2/2023 | Huitema et al. |
| 11,589,865 B2 | 2/2023 | Shelton, IV et al. |
| 11,701,114 B2 | 7/2023 | Shelton, IV et al. |
| 11,737,752 B2 | 8/2023 | Schings et al. |
| 11,766,257 B2 | 9/2023 | Shelton, IV et al. |
| 11,849,944 B2 | 12/2023 | Shelton, IV et al. |
| 2007/0045379 A1 * | 3/2007 | Shelton ............ A61B 17/07207 227/176.1 |
| 2007/0175955 A1 | 8/2007 | Shelton et al. |
| 2011/0101067 A1 * | 5/2011 | Johnson ............... A61B 17/068 227/176.1 |
| 2014/0001231 A1 | 1/2014 | Shelton, IV et al. |
| 2014/0263552 A1 | 9/2014 | Hall et al. |
| 2015/0134077 A1 | 5/2015 | Shelton, IV et al. |
| 2017/0056006 A1 * | 3/2017 | Shelton, IV ........... A61B 17/32 |
| 2018/0132849 A1 | 5/2018 | Miller et al. |
| 2018/0168615 A1 | 6/2018 | Shelton, IV et al. |
| 2018/0168650 A1 * | 6/2018 | Shelton, IV ........... A61B 34/30 |
| 2019/0105047 A1 | 4/2019 | Nalagatla et al. |
| 2019/0314017 A1 * | 10/2019 | Huitema ............... A61B 17/068 |
| 2021/0186495 A1 * | 6/2021 | Shelton, IV ..... A61B 17/07207 |
| 2022/0031320 A1 | 2/2022 | Hall et al. |
| 2022/0031351 A1 | 2/2022 | Moubarak et al. |
| 2022/0047265 A1 | 2/2022 | Miller et al. |
| 2022/0167980 A1 * | 6/2022 | Shelton, IV ..... A61B 17/07207 |
| 2022/0273299 A1 * | 9/2022 | Shelton, IV ........... G16H 40/63 |
| 2022/0304679 A1 | 9/2022 | Bakos et al. |
| 2022/0346858 A1 | 11/2022 | Aronhalt et al. |
| 2023/0119119 A1 | 4/2023 | Moubarak |

FOREIGN PATENT DOCUMENTS

| | | |
|---|---|---|
| CN | 105997173 A | 10/2016 |
| CN | 106036848 A | 10/2016 |
| CN | 108542454 A | 9/2018 |
| CN | 111195142 A | 5/2020 |

OTHER PUBLICATIONS

U.S. Food and Drug Administration 510(k) Premarket Notification, https://www.accessdata.fda.gov/scripts/cdrh/cfdocs/cfpmn/pmn.cfm?ID=K182476, last update: Jan. 8, 2024, 1 page.

* cited by examiner

PAN-LESS STAPLE CARTRIDGE ASSEMBLY COMPRISING RETENTION FEATURES FOR HOLDING STAPLE DRIVERS AND SLED

BACKGROUND

The present invention relates to surgical instruments and, in various arrangements, to surgical stapling and cutting instruments and staple cartridges for use therewith that are designed to staple and cut tissue.

SUMMARY

A staple cartridge assembly for use with a surgical stapling instrument is disclosed. The staple cartridge assembly comprises a plurality of staples, a plurality of staple drivers, and a cartridge body comprising a proximal end, a distal end, a longitudinal axis extending between the proximal end and the distal end, a deck configured to support patient tissue, a longitudinal cartridge slot configured to receive at least a portion of a firing driver of the surgical stapling instrument during a firing stroke, a plurality of staple cavities defined in the deck, wherein the staples are removably stored within the staple cavities, a plurality of staple drivers movable within the staple cavities, and a retention feature. The staple cartridge assembly further comprises a sled movable longitudinally through the cartridge body from a proximal unfired position to a distal fired position during a firing stroke, wherein the sled comprises a ramp configured to lift the staple drivers toward the deck to eject the staples from the staple cavities during the firing stroke, wherein the sled comprises a longitudinally-extending slot, wherein the retention feature supports at least one of the staple drivers in an unlifted position, and wherein the longitudinally-extending slot of the sled is configured to receive the retention feature during the firing stroke.

LISTING OF THE FIGURES

Various features of the embodiments described herein, together with advantages thereof, may be understood in accordance with the following description taken in conjunction with the accompanying drawings as follows.

Figure 15:
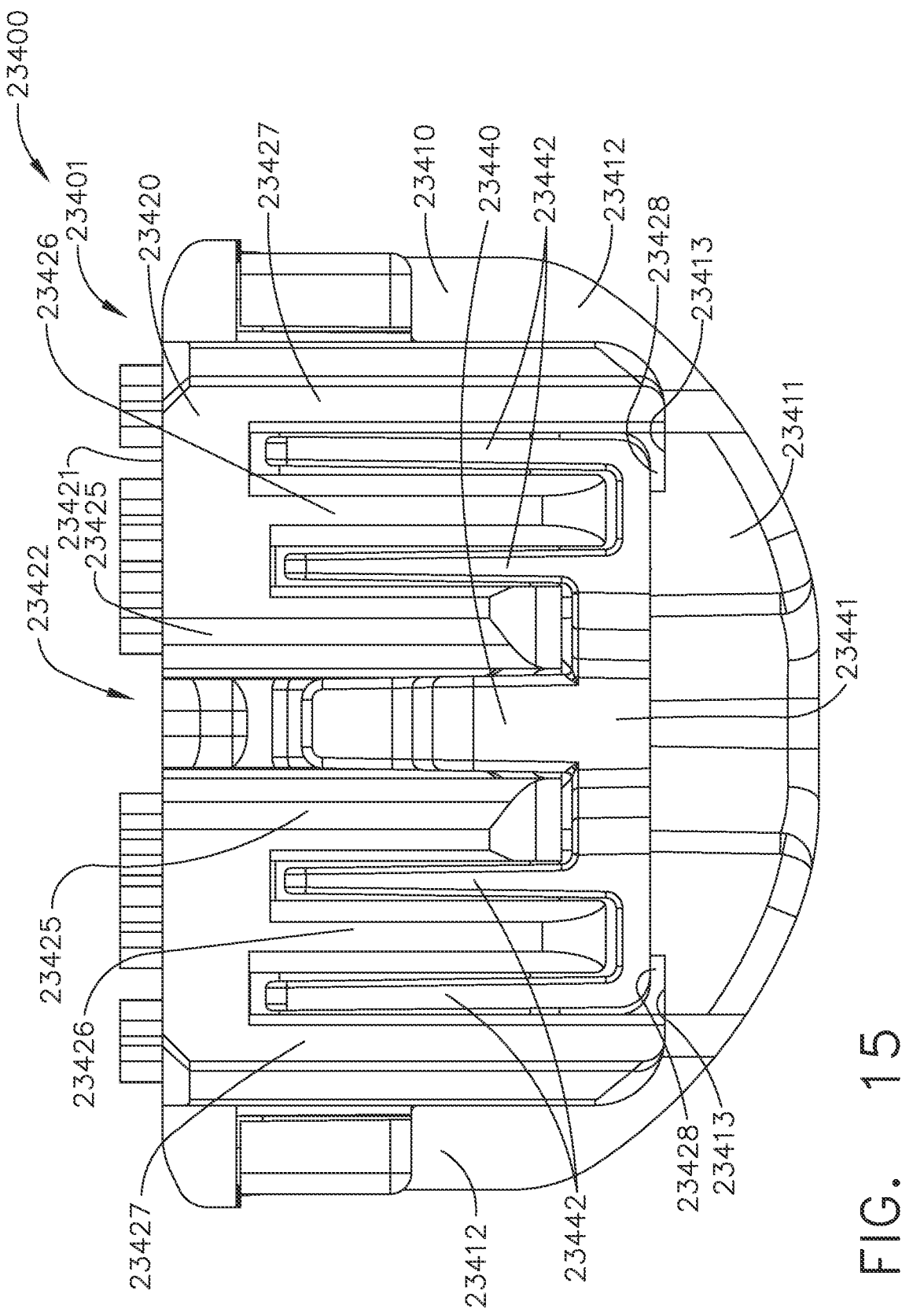
Figure 16:
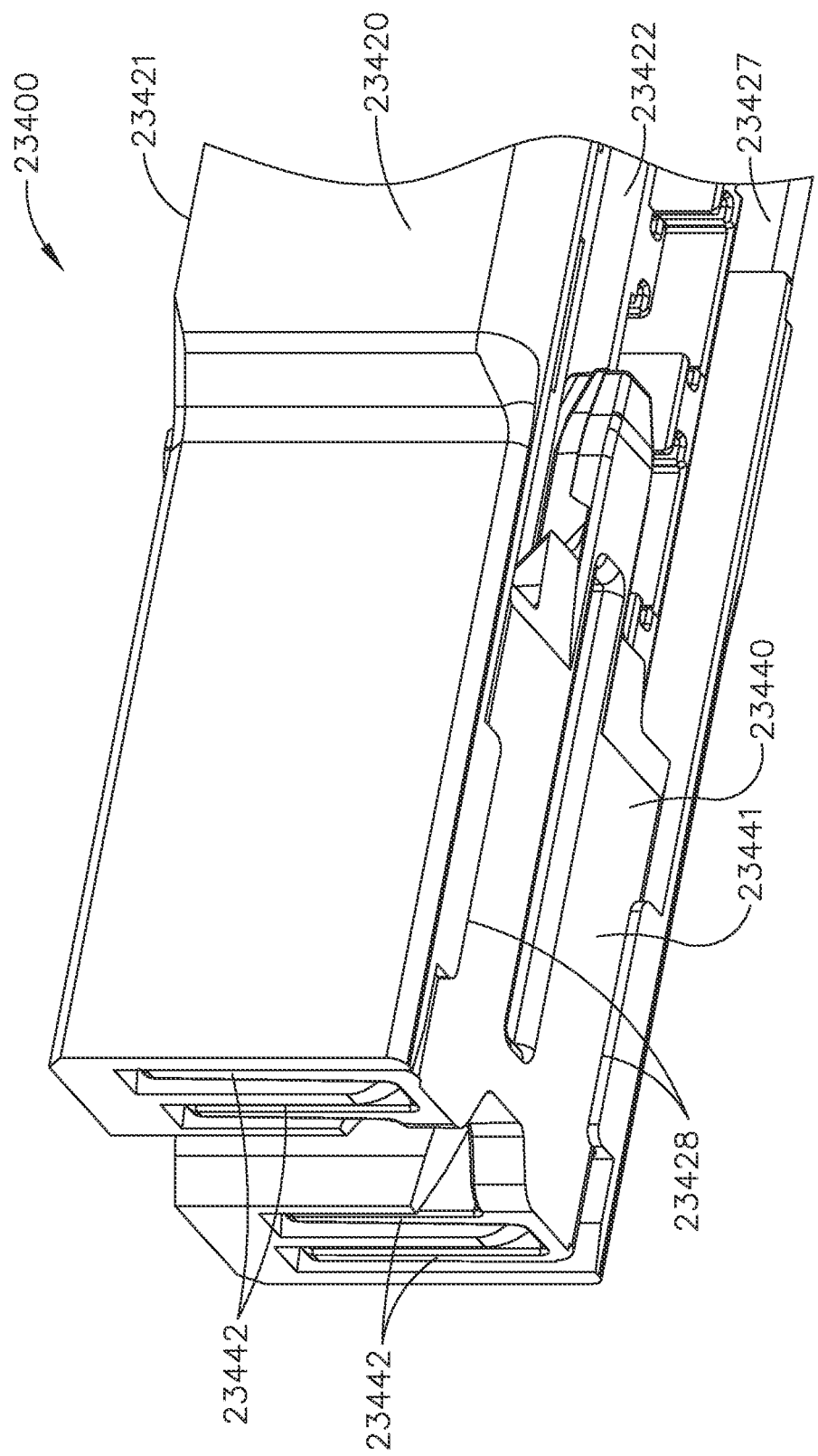

FIG. 15 is an end view of a surgical stapling assembly comprising a cartridge channel and a staple cartridge installed within the cartridge channel in accordance with the present disclosure, wherein the staple cartridge comprises a cartridge body and a sled; and FIG. 16 is a partial perspective view of the staple cartridge of FIG. 15, wherein the cartridge body comprises outer walls each comprising a retention feature extending laterally inward toward a longitudinal slot of the cartridge body to hold the sled in an unfired position.

Corresponding reference characters indicate corresponding parts throughout the several views.

DETAILED DESCRIPTION

Applicant of the present application owns the following U.S. Patent Applications that were filed on Oct. 13, 2023 and which are each herein incorporated by reference in their respective entireties:

U.S. patent application Ser. No. 18/379,759, titled METHOD OF OPERATING A SURGICAL STAPLING INSTRUMENT;

U.S. patent application Ser. No. 18/379,762, titled SURGICAL STAPLING SYSTEMS WITH ADAPTIVE STAPLE FIRING ALGORITHMS;

U.S. patent application Ser. No. 18/379,763, titled LEARNED TRIGGERS FOR ADAPTIVE CONTROL OF SURGICAL STAPLING SYSTEMS;

U.S. patent application Ser. No. 18/379,766, titled CONTROL CIRCUIT FOR ACTUATING MOTORIZED FUNCTION OF SURGICAL STAPLING INSTRUMENT UTILIZING INERTIAL DRIVE TRAIN PROPERTIES;

U.S. patent application Ser. No. 18/379,768, titled PROPORTIONATE BALANCING OF THE FUNCTION IMPACT MAGNITUDE OF BATTERY OUTPUT TO PEAK MOTOR CURRENT;

U.S. patent application Ser. No. 18/379,771, titled MOTOR OPTIMIZATION BY MINIMIZATION OF

PARASITIC LOSSES AND TUNING MOTOR DRIVE CONFIGURATION;

U.S. patent application Ser. No. 18/379,993, titled APPARATUS AND METHOD TO REDUCE PARASITIC LOSSES OF THE ELECTRICAL SYSTEM OF A SURGICAL INSTRUMENT;

U.S. patent application Ser. No. 18/379,776, titled SURGICAL TOOL WITH RELAXED FLEX CIRCUIT ARTICULATION;

U.S. patent application Ser. No. 18/379,777, titled WIRING HARNESS FOR SMART STAPLER WITH MULTI AXIS ARTICULATION;

U.S. patent application Ser. No. 18/379,781, titled SURGICAL SYSTEM WITH WIRELESS ARRAY FOR POWER AND DATA TRANSFER; and U.S. patent application Ser. No. 18/379,784, titled SURGICAL STAPLE CARTRIDGE COMPRISING REPLACEABLE ELECTRONICS PACKAGE.

Applicant of the present application owns the following U.S. Patent Applications that were filed on Oct. 13, 2023 and which are each herein incorporated by reference in their respective entireties:

U.S. patent application Ser. No. 18/379,790, titled METHOD OF ASSEMBLING A STAPLE CARTRIDGE;

U.S. patent application Ser. No. 18/379,793, titled CONTROL SURFACES ON A STAPLE DRIVER OF A SURGICAL STAPLE CARTRIDGE;

U.S. patent application Ser. No. 18/379,796, titled INTEGRAL CARTRIDGE STIFFENING FEATURES TO REDUCE CARTRIDGE DEFLECTION;

U.S. patent application Ser. No. 18/379,801, titled STAPLE CARTRIDGE COMPRISING WALL STRUCTURES TO REDUCE CARTRIDGE DEFLECTION;

U.S. patent application Ser. No. 18/379,805, titled STAPLE CARTRIDGE COMPRISING A SLED HAVING A DRIVER LIFT CAM;

U.S. patent application Ser. No. 17/379,808, titled SURGICAL STAPLE CARTRIDGES WITH SLEDS CONFIGURED TO BE COUPLED TO A FIRING DRIVER OF A COMPATIBLE SURGICAL STAPLER;

U.S. patent application Ser. No. 18/379,810, titled STAPLE CARTRIDGE COMPRISING A COMPOSITE SLED;

U.S. patent application Ser. No. 18/379,811, titled SURGICAL INSTRUMENTS WITH JAW AND FIRING ACTUATOR LOCKOUT ARRANGEMENTS LOCATED PROXIMAL TO A JAW PIVOT LOCATION;

U.S. patent application Ser. No. 18/379,815, titled SURGICAL INSTRUMENTS WITH LATERALLY ENGAGEABLE LOCKING ARRANGEMENTS FOR LOCKING A FIRING ACTUATOR;

U.S. patent application Ser. No. 18/379,817, titled DUAL INDEPENDENT KEYED LOCKING MEMBERS ACTING ON THE SAME DRIVE MEMBER;

U.S. patent application Ser. No. 18/379,820, titled ADJUNCTS FOR USE WITH SURGICAL STAPLING INSTRUMENTS;

U.S. patent application Ser. No. 18/379,822, titled ADJUNCTS FOR USE WITH SURGICAL STAPLING INSTRUMENTS;

U.S. patent application Ser. No. 18/379,826, titled JAW CONTROL SURFACES ON A SURGICAL INSTRUMENT JAW;

U.S. patent application Ser. No. 18/379,827, titled ZONED ALGORITHM ADAPTIVE CHANGES BASED ON CORRELATION OF COOPERATIVE COMPRESSION CONTRIBUTIONS OF TISSUE;

U.S. patent application Ser. No. 18/379,831, titled STAPLE CARTRIDGES COMPRISING TRACE RETENTION FEATURES; and U.S. patent application Ser. No. 18/379,832, titled STAPLE CARTRIDGES COMPRISING STAPLE RETENTION FEATURES.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

FIGS. 1-6 depict a surgical stapling assembly 23000 configured to clamp, cut, and staple patient tissue during a surgical stapling procedure. The surgical stapling assembly 23000 comprises a shaft 23010, a cartridge channel jaw 23020, and an anvil jaw 23030 movable relative to the cartridge channel jaw 23020 to clamp patient tissue therebetween. The cartridge channel jaw 23020 may be movable relative to the anvil jaw 23030. The surgical stapling assembly 23000 further comprises a staple cartridge 23050 configured to be installed into a cartridge channel 23021 of the cartridge channel jaw 23020. The surgical stapling assembly 23000 further comprises a firing driver 23040 actuatable, or movable distally, relative to the cartridge channel jaw 23020 and the anvil jaw 23030. The firing driver 23040 may comprise an I-beam head comprising opposing jaw-camming members that is movable distally to staple and cut patient tissue captured between the staple cartridge assembly 23050 and the anvil jaw 23030 during a staple firing stroke.

The surgical stapling assembly 23000 may be coupled to any suitable actuation interface such as, for example, a surgical robot and/or a surgical instrument handle that is actuatable to control the operation of the surgical stapling assembly 23000.

The cartridge channel 23021 comprises a bottom portion 23022 and channel sidewalls 23024 extending upwardly from the bottom portion 23022 defining a channel cavity 23025 within which the staple cartridge 23050 is configured to be installed. The cartridge channel 23021 further comprises a longitudinal slot 23023 defined therein that is configured to receive at least a portion of the firing driver 23040 during the staple firing stroke. The anvil jaw 23030 comprises a tissue compression surface 23031, a plurality of forming pockets 23032, and a longitudinal slot 23033 configured to receive at least a portion of the firing driver 23040 during the staple firing stroke. Further to the above, the longitudinal slot 23023 of the cartridge jaw 23020 and the longitudinal slot 23033 of the anvil jaw 23030 are each configured to receive a jaw-camming member of the firing driver 23040, for example, during the staple firing stroke. The jaw-camming members are configured to hold the jaws 23020, 23030 in a clamped position during the firing stroke; however, in accordance with the present disclosure, a firing driver may not comprise jaw-camming members.

As discussed above, the staple cartridge assembly 23050 is configured to be installed in the cartridge channel jaw 23020. The staple cartridge 23050 comprises a cartridge body 23051, a sled 23080 movable from a proximal end 23055 of the cartridge body 23051 to a distal end 23056 of the cartridge body 23051 during a staple firing stroke, and a plurality of staple drivers 23090 liftable by the sled 23080 from an unfired position (FIG. 3) to a fired position to lift staples 23001 supported on the staple drivers 23090 toward the anvil jaw 23030 during the staple firing stroke. The staples 23001 are removably stored within the cartridge body 23051 and are configured to be formed by the forming pockets 23032 defined in the anvil jaw 23030. The cartridge body 23051 comprises a longitudinal slot 23054 configured to receive at least a portion of the firing driver 23040 during the staple firing stroke, a deck surface 23052 configured to support patient tissue thereon, and a plurality of staple cavities 23053 configured to removably store the staples 23001 therein. The sled 23080 is actuatable through the cartridge body 23051 to cammingly lift the staple drivers 23090 relative to the cartridge body 23051 to eject the staples 23001 from the staple cavities 23053.

Figure 1:
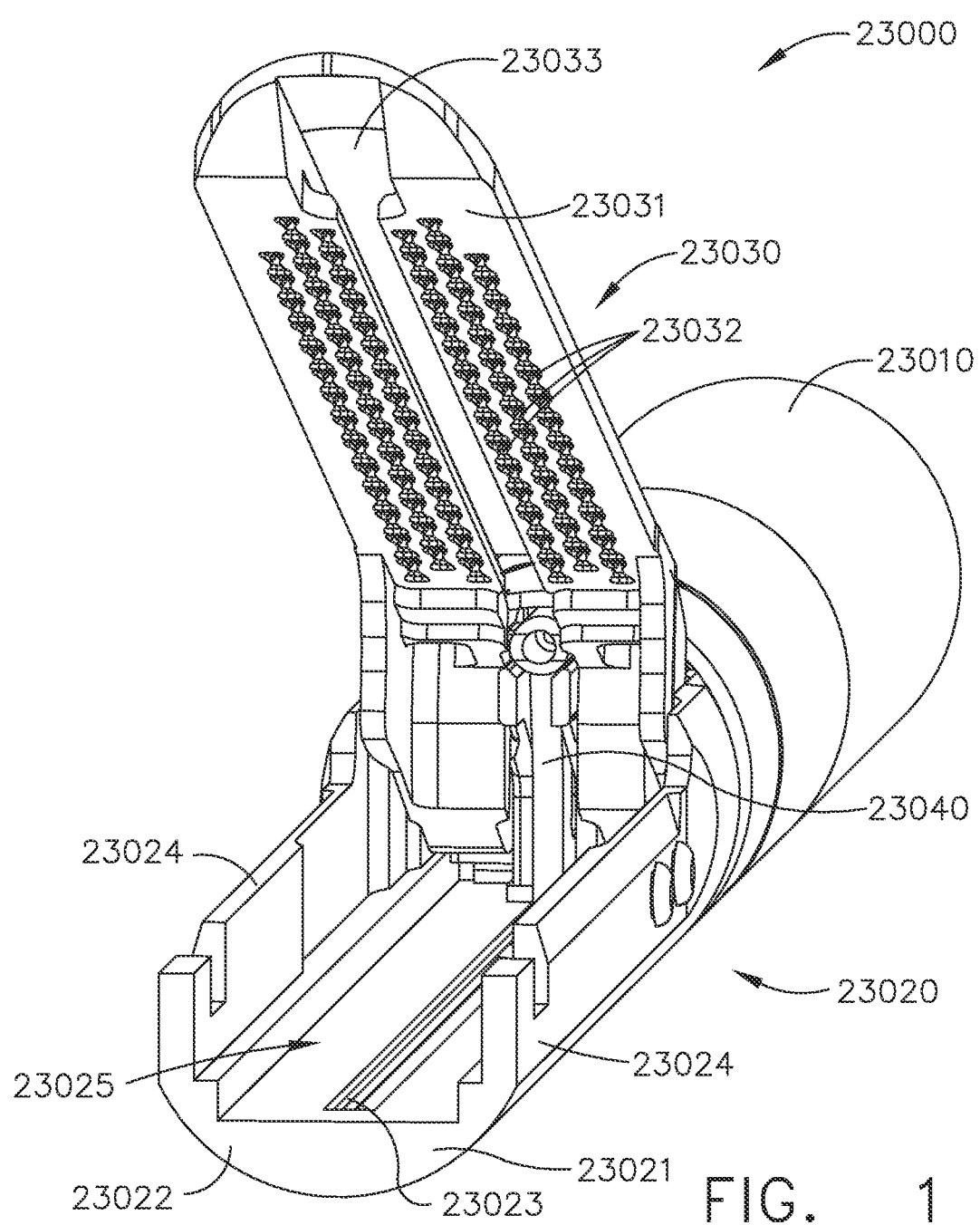
FIG. 1 is a perspective view of a surgical stapling assembly comprising a shaft, a cartridge channel jaw configured to receive a staple cartridge therein, and an anvil jaw movable relative to the cartridge channel jaw in accordance with the present disclosure.
Figure 2:
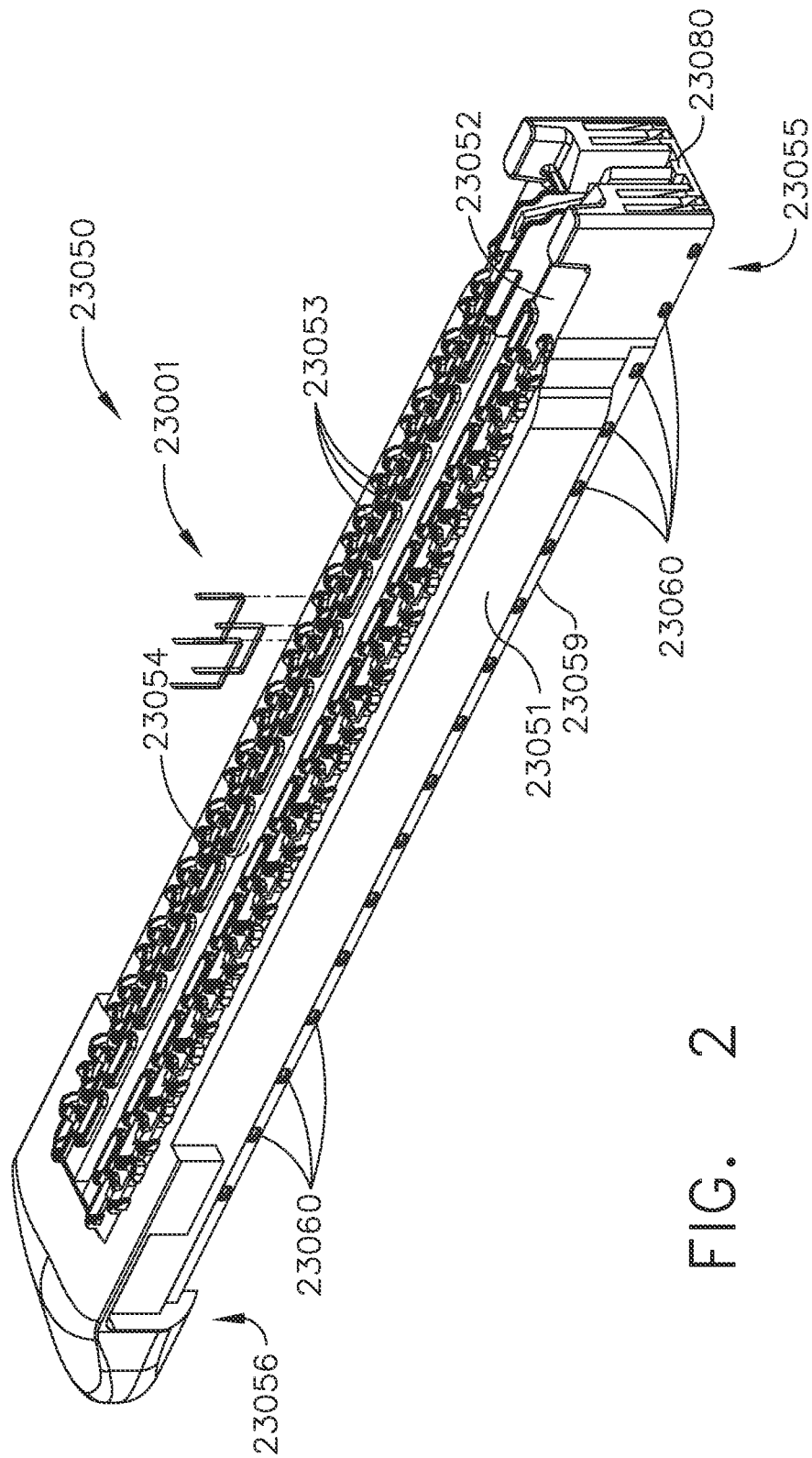
FIG. 2 is a perspective view of a staple cartridge for use with the surgical stapling assembly of FIG. 1 in accordance with the present disclosure, wherein the staple cartridge comprises a cartridge body, a plurality of staples, a plurality of staple drivers, and a sled.

Referring to FIG. 2, the staple cartridge 23050 is pan-less. In other words, the staple cartridge 23050 does not comprise a pan that extends around the bottom of the cartridge body 23051 that prevents the staple drivers 23090 and/or the sled 23080 from falling out of the bottom of the cartridge body 23051. Discussed in greater detail below, the staple cartridge 23050 further comprises retention features, such as retention features 23060, for example, configured to prevent the staple drivers 23090 and the sled 23080 from falling out of the bottom of the cartridge body 23051. As also discussed in greater detail below, the retention features 23060 are also configured to guide the sled 23080 as the sled 23080 is moved distally through the cartridge body 23051 during the staple firing stroke.

Figure 4:
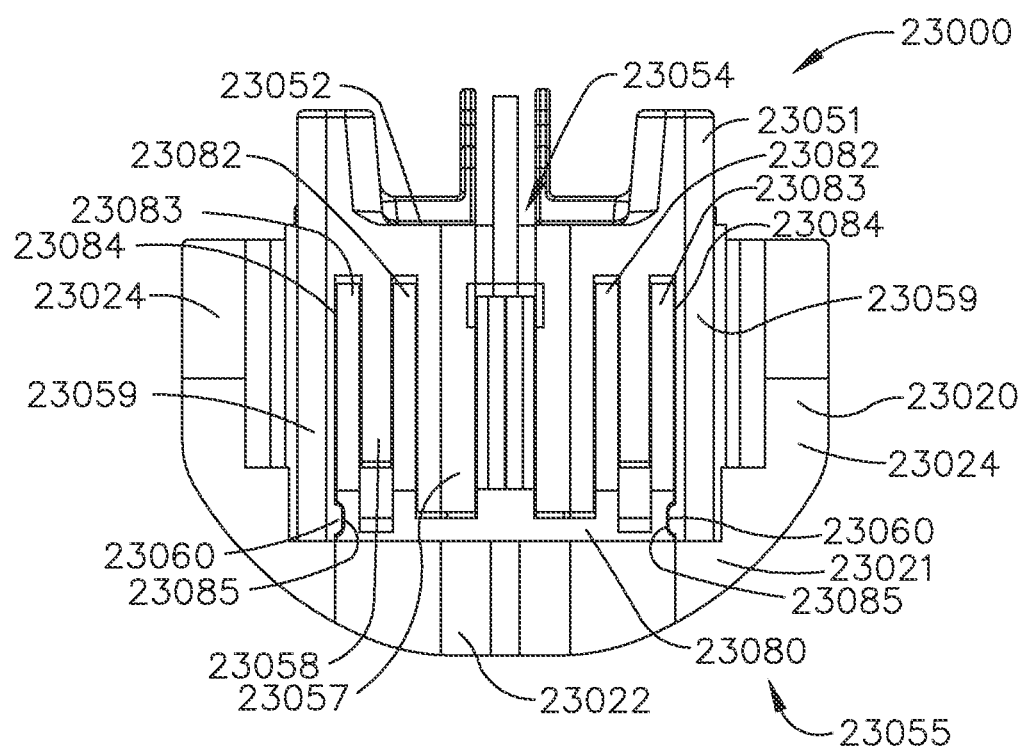
FIG. 4 is a cross-sectional end view of the proximal end of the surgical stapling assembly of FIG. 1 illustrated with some components removed.

Referring to FIG. 4, the cartridge body 23051 further comprises a plurality of cartridge walls comprising inner walls 23057 defining the longitudinal slot 23054, intermediate walls 23058, and outer walls 23059 that are positioned against and supported by the channel sidewalls 23024 when the staple cartridge 23050 is seated in the cartridge jaw 23020. The sled 23080 comprises a bottom portion 23081 and a central rib 23086 extending upwardly from the bottom portion 23081 that is configured to be received within the longitudinal slot 23054 of the cartridge body 23051. The central rib 23086 comprises a knife 23087 configured to cut tissue as the sled 23080 is moved distally during the staple firing stroke. The sled 23080 further comprises inner ramp wedges 23082 extending upwardly from the bottom portion 23081 and outer ramp wedges 23083 extending upwardly from the bottom portion 23081. The ramp wedges 23082, 23083 are configured to lift the staple drivers 23090 relative to the cartridge body 23051 during the staple firing stroke to drive the staples supported thereon. Discussed in greater detail below, the outer ramped wedges comprise outer walls 23084 including retention slots, notches, and/or grooves, 23085 defined therein configured to guide the sled 23080 within the cartridge body 23051 during the staple firing stroke and hold the sled 23080 in the cartridge body 23051.

Figure 3:
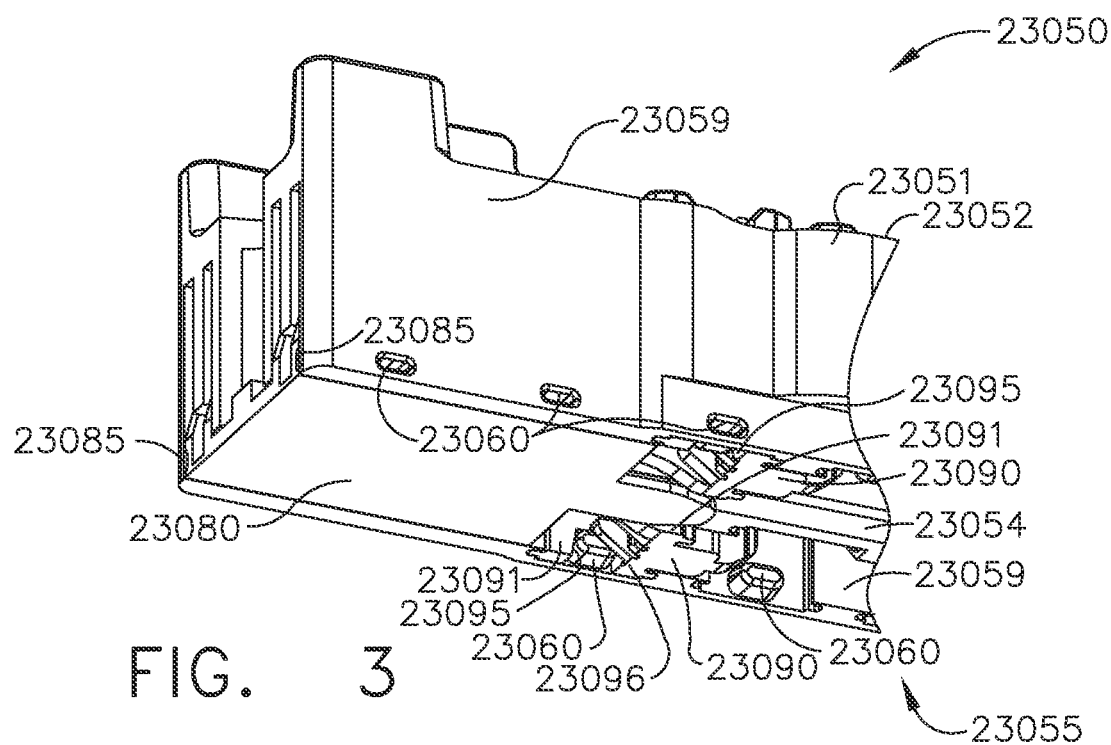
FIG. 3 is a perspective view of a proximal end of the staple cartridge of FIG. 2, wherein the staple cartridge further comprises a plurality of retention features configured to prevent the staple drivers from falling out of the bottom of the cartridge body and configured to guide the sled as the sled is moved distally through a staple firing stroke.
Figure 6:
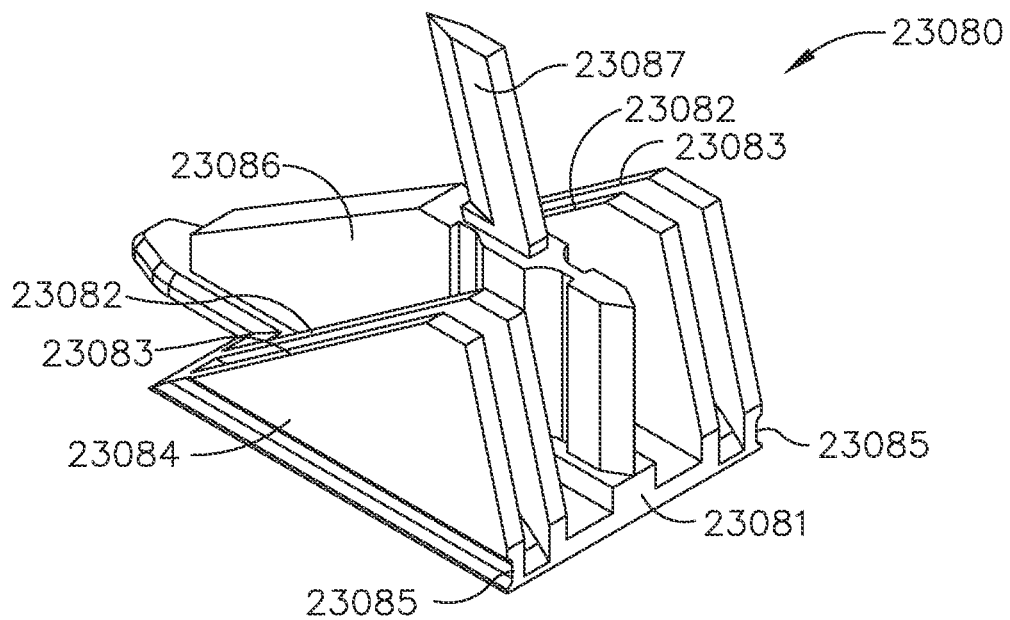
FIG. 6 is a perspective view of the sled of the staple cartridge of FIG. 2.

As discussed above, the retention features 23060 are configured to prevent the staple drivers 23090 and the sled 23080 from falling out of the bottom of the cartridge body 23051. The retention features 23080 are arranged in a longitudinal array on each lateral side of the cartridge body 23051. Referring to FIG. 3, each side of the cartridge body 23051 has at least one retention feature 23090 configured to releasably hold the sled 23080 in its proximal unfired position. When the sled 23080 is pushed distally by the firing driver, the sled 23080 releases from the proximal-most retention features 23090 so that the sled 23080 can be advanced distally through the staple firing stroke. Each other retention feature 23060 is configured to hold a staple driver 23090 in an unlifted position and, as the sled 23080 passes thereby, release the staple driver 23090 so that the sled 23080 can lift the staple driver 23090 into a fired position. Such retention features 23060 also hold and guide the sled 23080 in the cartridge body 23051. Each retention feature 23060 comprises at least one protrusion extending inwardly toward the longitudinal slot 23054 from an outer wall 23059; however, the retention features 23060 can comprise any suitable configuration. Referring to FIG. 6, the retention features 23060 extend into notches 23085 defined in the sled 23080 which prevent the sled 23080 from falling out of the bottom of the cartridge body 23051. As can be seen in FIG. 6, the notches 23085 extend the entire longitudinal length of the sled 23080 so as to allow the sled 23080 to simultaneously engage two or more retention features 23060 at all points during the staple firing stroke, as discussed in greater detail below.

Figure 5:
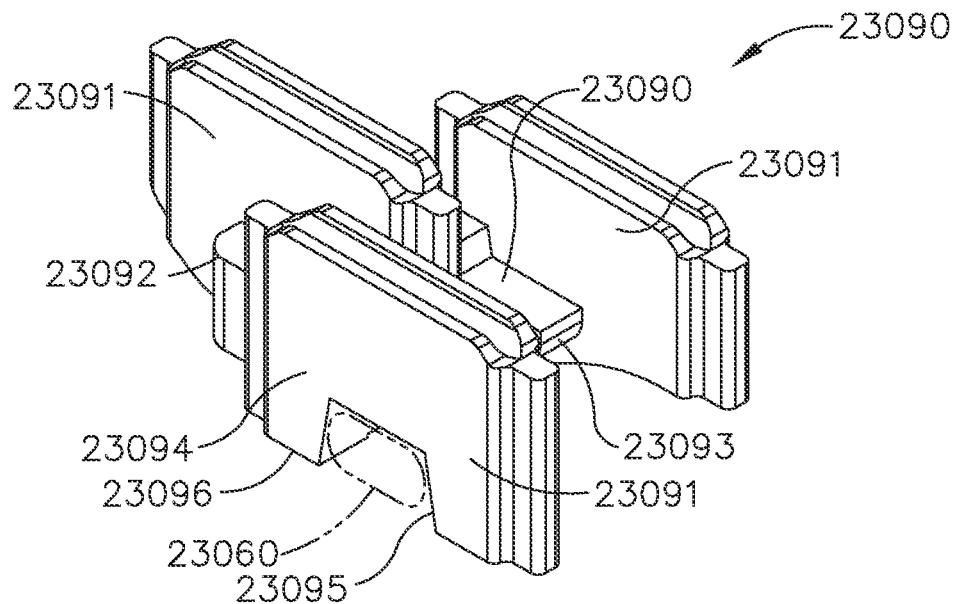
FIG. 5 is a perspective view of one of the staple drivers of the staple cartridge of FIG. 2.

Referring to FIG. 5, each staple driver 23090 comprises a plurality of staple support columns 23091 configured to support the staples 23001 thereon and web portions 23092 connecting the staple support columns 23091. Each support column 23091 comprises a seat, or cradle, that receives a base of a staple 23001. Each staple driver 23090 further comprises at least one lift cam surface 23093 configured to be engaged by the ramp wedges 23082, 23083 of the sled 23080 during the staple firing stroke to lift the staple driver 23090 relative to the cartridge body 23051. Each staple driver 23090 comprises an outer driver wall 23094 defined by the staple support column 23091 nearest the outer wall 23059 of the cartridge body 23051. A notch 23095 is defined in the outer driver wall 23094 and is configured to receive a retention feature 23060 therein when the staple driver 23090 is in its unfired, or unlifted, position such that the retention feature 23060 holds the staple driver 23090 in the cartridge body 23051 without a cartridge pan extending under the bottom of the cartridge body 23051. As the staple drivers 23090 are lifted upwardly by the sled 23080, the staple drivers 23090 disengage from the retention features 23060.

Further to the above, referring again to FIG. 3, two retention features 23060 releasably hold the sled 23080 in its unfired position; however, any suitable number of retention features 23060 are contemplated for holding the sled 23080 in its unfired position. As can also be seen in FIG. 3, retention features 23060 extend inwardly from the outer walls 23059 into the staple cavities 23053. Such retention features 23060, as discussed above, are configured to hold the staple drivers 23090 in their unfired positions and support the sled 23080 during the staple firing stroke. Each staple driver 23090 can be held in its unfired, unlifted position using two retention features 23060—one extending laterally inwardly toward the longitudinal slot 23054 from the outer wall 23059 and one extending laterally outwardly toward the outer wall 23059 from the inner wall 23057. The retention feature 23060 extending laterally inwardly from the inner wall 23057 may fit within a corresponding notch defined in an inner wall of a staple support column 23091 adjacent the inner wall 23057 of the cartridge body 23051.

As the sled 23080 is actuated through the staple firing stroke, the ramp wedges 23082, 23083 of the sled 23080 lift the staple drivers 23090 from their unfired, unlifted position to a fired, lifted position to eject the staples 23001 from the cartridge body 23051. As the ramp wedges 23082, 23083 lift the staple drivers 23090, the notches 23085 defined in the sled 23080 are engaged with one or more retention features 23060 such that the retention features 23060 guide the sled 23080 through the firing stroke and hold the sled 23080 in the cartridge body 23051. In accordance with the present disclosure, at least two retention features 23060 may engage with the sled 23080 for any given position of the sled 23080 along its firing stroke. Further, more than two retention features 23060 may engage with the sled 23080 for any given position of the sled 23080. The sled 23080 can simultaneously lift two or more staples 23001 in each outer longitudinal row of staple cavities and can be concurrently engaged with the retention features 23060 associated with the staple drivers 23090 being driven, or lifted.

Further to the above, the retention features 23060 can be created using any suitable process. Referring to FIG. 3, the creation of the retention features 23060 in the cartridge body 23051 may create divots, recesses, and/or dimples in the outside lateral surfaces of the cartridge body 23051 that, as discussed below, can be used to advantageous effect. For instance, the channel sidewalls 23024 of the cartridge jaw comprise bumps that that are aligned with, and received within, the divots when the staple cartridge 23050 is installed in the channel cavity 23025 that releasably hold the staple cartridge 23050 in the channel cavity 23025. Moreover, the bumps extending from the channel sidewalls 23024 support the retention features 23060 which, among other things, assist in preventing the staple drivers 23090 from releasing prematurely. With or without such bumps, the width of the staple cartridge 23050 can be configured such that the retention features 23060 are at least partially squeezed inwardly by the channel sidewalls 23024 upon the installation of the staple cartridge 23050 into the cartridge channel 23021.

The retention features 23060 may be formed using a thermoplastic heat staking process. The retention features 23060 may be formed after the installation of the staple drivers 23090 into the cartridge body 23051. The retention features 23060 may be formed before the staple drivers 23090 are installed into the cartridge body 23051. The staple drivers 23090 can be pressed up into the staple cavities 23053 from the bottom of the cartridge body 23051 and the retention features 23060 flex laterally outwardly until the staple drivers 23090 are fully installed in the cartridge body 23051. At such point, the retention features 23060 can reassume their original position, or at least resiliently return toward their original position, to hold the staple drivers 23090 in the cartridge body 23051.

Such retention features can help reduce the tendency of a sled and/or staple drivers to become dislodged from the staple cartridge prior to the staple cartridge being installed in the stapling instrument. When a fired staple cartridge assembly is uninstalled from the cartridge channel, moreover, the retention features can prevent the already-fired staple drivers from falling out of the bottom of the cartridge body. Additionally, the sled of the staple cartridge can be configured to be slid into the proximal end of the cartridge body. The notches defined in the sled and corresponding retention features can align the sled relative to the cartridge body when the sled is installed into the cartridge body.

Figure 7:
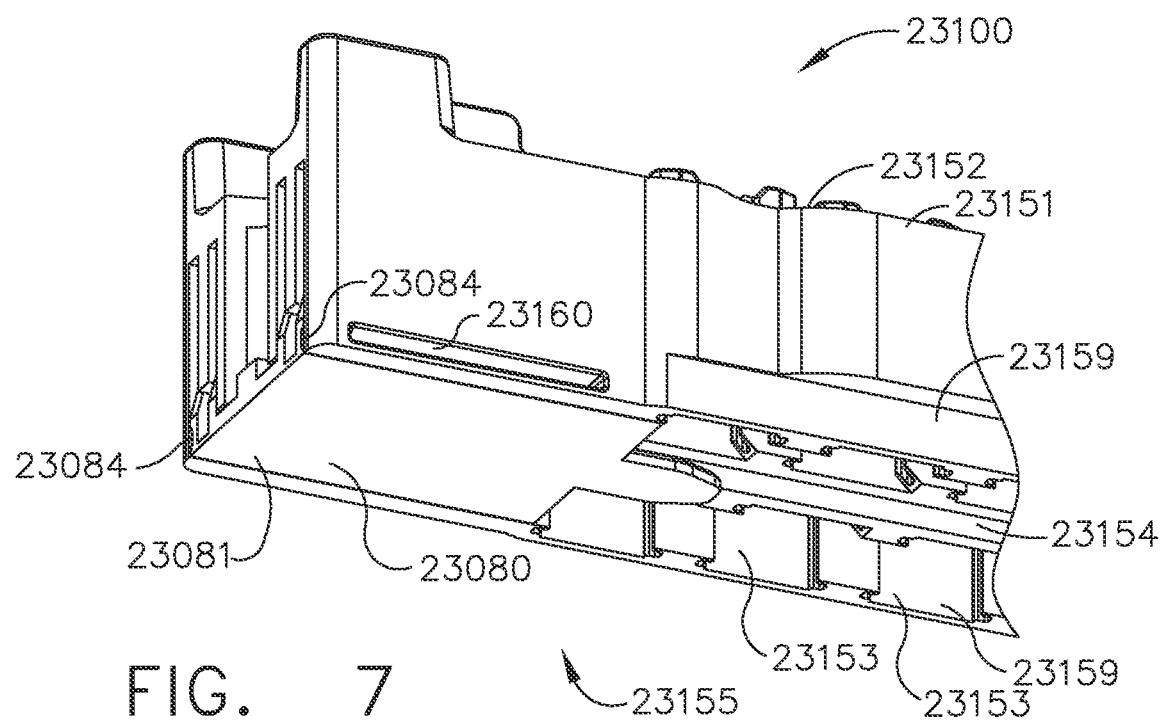
FIG. 7 is a perspective view of a proximal end of a staple cartridge in accordance with the present disclosure comprising a retention feature configured to hold a sled in an unfired position and configured to guide the sled during a portion of the firing stroke.

FIG. 7 is a partial perspective view of a staple cartridge 23100 comprising a cartridge body 23151 and the sled 23080. The cartridge body 23151 comprises a deck 23152, a plurality of staple cavities 23153, and a longitudinal slot 23154. The cartridge body 23151 further comprises a proximal end 23155 and outer cartridge body walls 23159. The outer cartridge body walls 23159 comprise elongate retention features, or rails, 23160 extending laterally inwardly toward the longitudinal slot 23154. The notches 23085 of the sled 23080 receive the retention rails 23160 in the unfired, or unadvanced, position of the sled 23080. In accordance with the present disclosure, the retention rails 23160 may be formed using a thermoplastic heat staking process, for example, that pushes inwardly on the outside walls 23159 of the cartridge body 23151. In any event, the retention rails 23160 support the sled 23080 in its proximal unfired position and also guide the sled 23080 during the initial part of the staple firing stroke. The cartridge body 23151 may further comprise retention features 23060 that releasably hold the staple drivers in their unfired positions and support and guide the sled 23080 during the remainder of the staple firing stroke.

In accordance with the present disclosure, a sled of a staple cartridge may become dislodged when the staple cartridge is shipped and/or handled prior to being fully installed in a cartridge channel of a stapling instrument. For instance, the sled may be bumped distally when being handled by a technician and/or bumped distally against a firing member when the staple cartridge is installed proximally into a stapling instrument. As described in greater detail below, a staple cartridge is provided which may prevent the sled from being moved out of its unfired position until the staple cartridge is fully seated in a cartridge channel.

Figure 9:
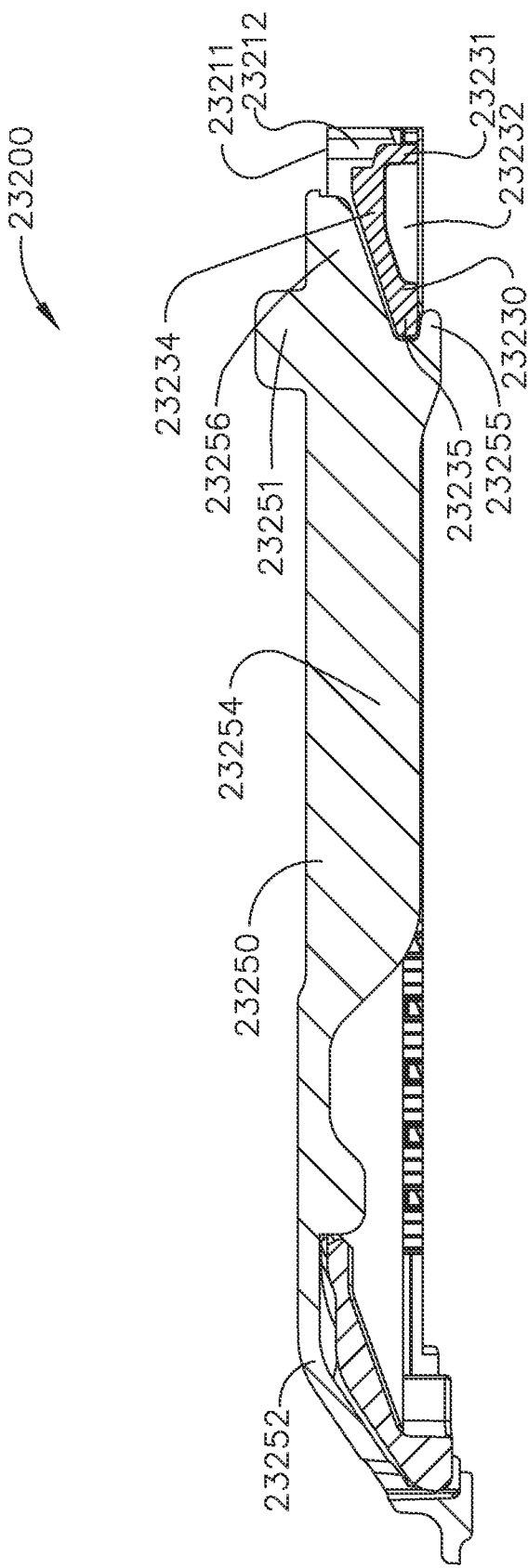
FIG. 9 is a cross-sectional view of the staple cartridge of FIG. 8, wherein the staple retainer comprises a central fin positioned within a longitudinal slot of the cartridge body and the central fin comprises a proximal hook.
Figure 10:
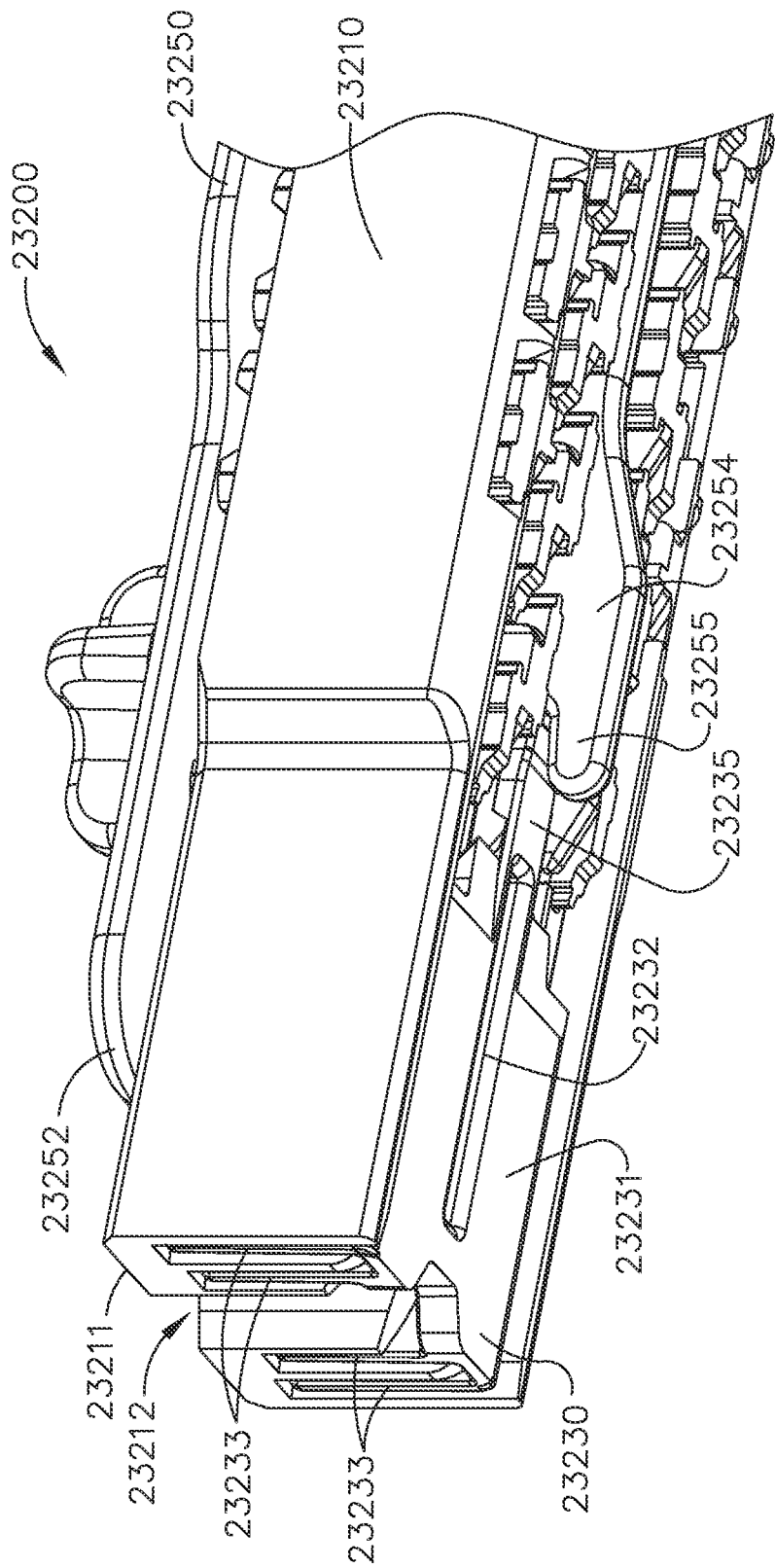
FIG. 10 is a partial perspective view of a proximal end of the staple cartridge of FIG. 8.
Figure 11:
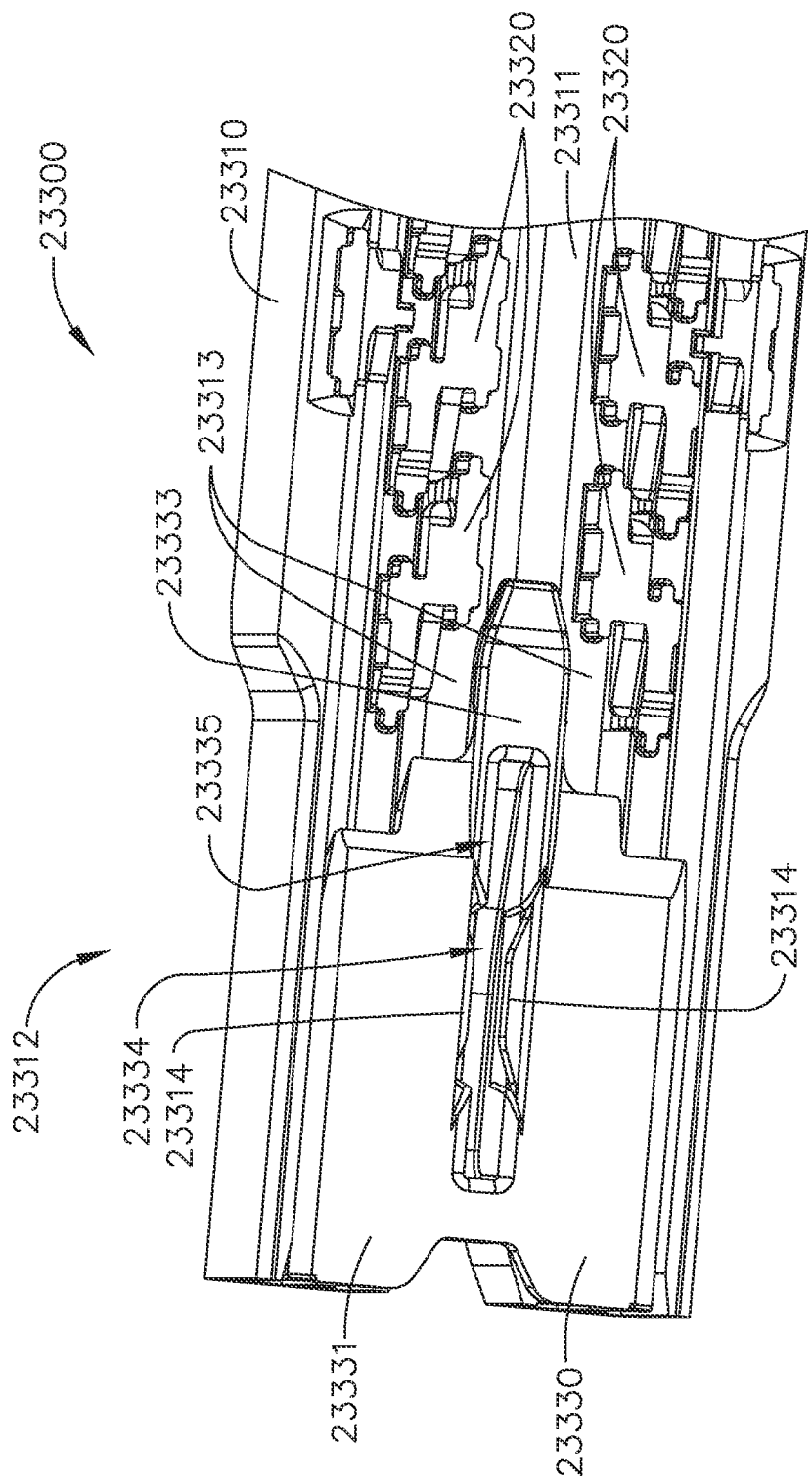
FIG. 11 is a perspective view of a proximal end of a staple cartridge in accordance with the present disclosure comprising a cartridge body and a sled positioned within the cartridge body in an unfired position, wherein the cartridge body comprises retention features engaged with the sled to hold the sled in the unfired position.
Figure 12:
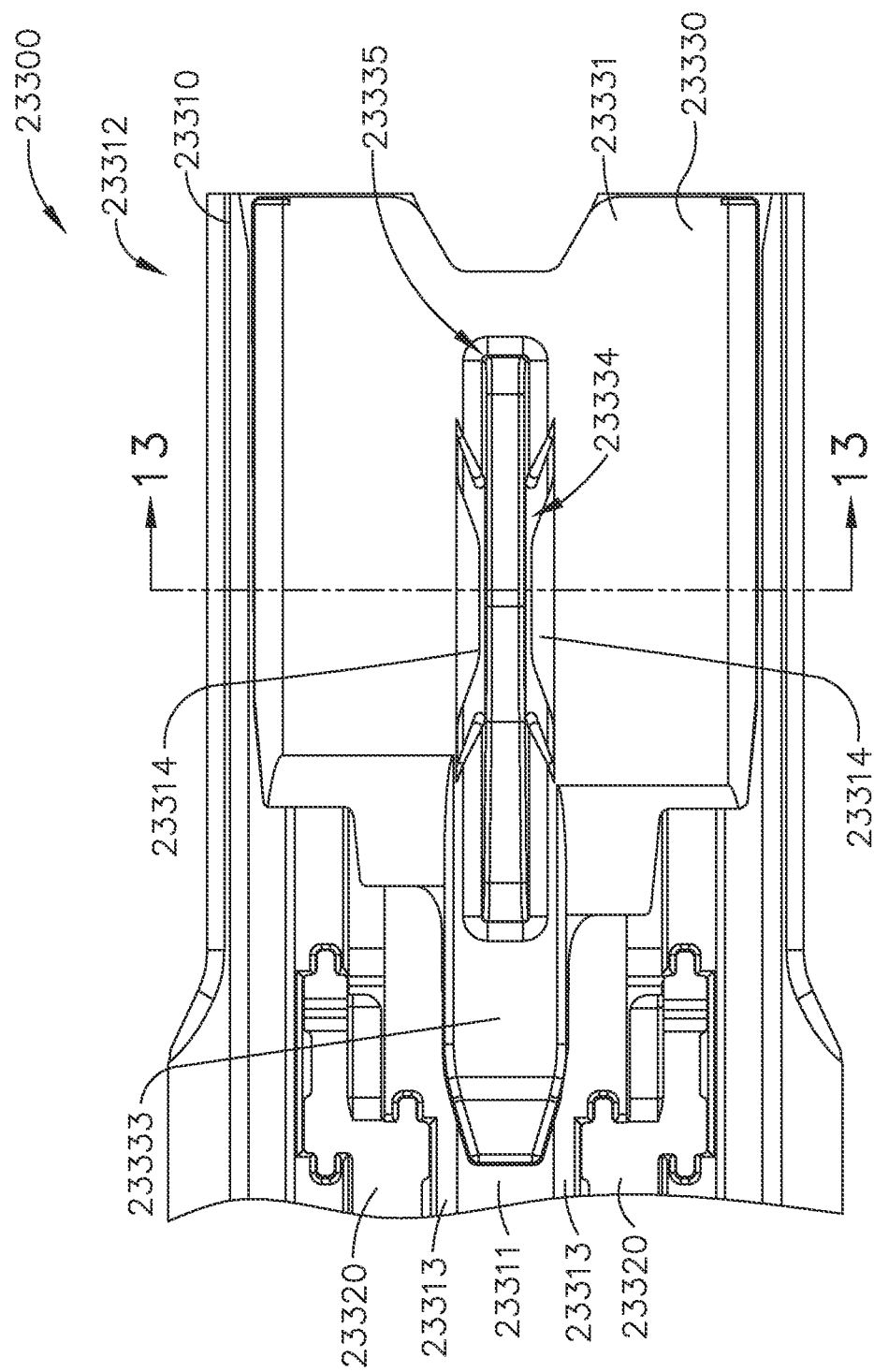
FIG. 12 is a bottom view of the proximal end of the staple cartridge of FIG. 11.

FIGS. 9-11 depict a staple cartridge 23200 for use with a surgical stapling assembly. The staple cartridge 23200 can be configured to be installed in a cartridge channel jaw of a surgical stapling assembly. The staple cartridge 23200 comprises a cartridge body 23210 and a plurality of staples removably stored in the cartridge body 23210 that are ejected from the cartridge body 23210 by a sled 23230 as the sled 23230 is translated through the cartridge body 23210 from an unfired position to a fired position during a staple firing stroke. The cartridge body 23210 comprises a cartridge deck 23211 and a longitudinal slot 23212 defined in the cartridge deck 23211 that is configured to receive at least a portion of the sled 23230 as well as a portion of a firing driver which pushes the sled 23230 distally during the staple firing stroke.

The sled 23230 comprises a bottom portion 23231 and a plurality of ramped wedges 23233 extending upwardly into the cartridge body 23210 from the bottom portion 23231. The ramped wedges 23233 are configured to lift staple drivers and eject staples from the cartridge body 23210 during the staple firing stroke. The sled 23230 further comprises a central rib 23234 configured to be received within the longitudinal slot 23212 and a distal nose portion 23235.

The staple cartridge 23200 further comprises a staple retainer 23250 that is installed onto, or attached to, the cartridge body 23210 prior to the staple cartridge 23200 being shipped to serve as a sterile barrier to staples positioned in the cartridge body 23210 and to prevent the staples from falling out of the top of the cartridge body 23210. The staple retainer 23250 is configured to be removed from the cartridge body 23210 prior to firing the staples of the staple cartridge 23200. In accordance with the present disclosure, the staple retainer 23250 can be removed after fully installing the staple cartridge 23200 in a cartridge channel jaw. A clinician can push downwardly on the staple retainer 23250 to seat the staple cartridge 23200 in the cartridge channel jaw. The staple retainer 23250 could also be removed prior to the staple cartridge 23200 being installed into a cartridge channel.

The staple retainer 23250 is positioned against the cartridge deck 23211 and comprises a proximal end 23251, a distal end 23252, and retention arms 23253 configured to releasably hold the staple retainer 23250 to the cartridge body 23210. The staple retainer 23250 further comprises a central fin 23254 extending down into the longitudinal slot 23212. The central fin 23254 comprises a proximal hook 23255 configured to engage the distal nose portion 23235 of the sled 23230 such that the staple retainer 23250 holds the sled 23230 in its unfired position and prevents the sled 23230 from falling out of the bottom of the cartridge body 23210. The central fin 23254 further comprises an upper ramped edge 23256 positioned adjacent the central rib 23234 that prevents the sled 23230 from being moved distally. In accordance with the present disclosure, a user can pry the staple retainer 23250 off of the cartridge body 23210 by lifting on the distal end 23252 of the staple retainer 23250 and rotating the staple retainer 23250 relative to the cartridge body 23210 and the sled 23230. This rotation can allow the staple retainer 23250 to disengage the distal nose portion 23235 of the sled 23230 so as to not accidentally disturb the position of the sled 23230 during removal of the staple retainer 23250. The user can pull the staple retainer 23250 distally relative to the sled 23230 when removing the staple retainer 23250 so as to not disturb the position of the sled 23230.

Regardless of the manner in which the staple retainer 23250 is detached from the cartridge body 23210, the staple retainer 23250 is configured to positively retain the sled 23230 in its unfired position by preventing vertical and longitudinal movement of the sled 23230 relative to the cartridge body 23210. Referring to FIG. 9, the sled 23230 comprises a retention slot, or recess, 23232 defined in the bottom thereof and the proximal hook 23255 is configured to be received within the retention slot 23232 when the staple retainer 23250 is attached to the cartridge body 23210. Such an arrangement can also prevent inadvertent proximal movement of the sled 23230 relative to the cartridge body 23210. The proximal hook 23255 can engage the sled 23230 in a snap-fit manner.

FIGS. 11-14 depict a staple cartridge 23300 that is configured to be installed in a cartridge channel of a surgical stapling assembly. The staple cartridge 23300 comprises a cartridge body 23310, a plurality of staple drivers 23320, and a plurality of staples configured to be ejected from the cartridge body 23310 by the staple drivers 23320 during a staple firing stroke. The staple cartridge 23300 further comprises a sled 23330 movable distally through the cartridge body 23310 from an unfired position (illustrated in FIGS. 11-14) to a fired position during the staple firing stroke to lift the staple drivers 23320 and eject the staples.

The cartridge body 23310 comprises a longitudinal slot 23311 configured to receive at least a portion of a firing driver therein. The cartridge body 23310 further comprises a proximal end 23312 within which the sled 23330 is positioned in an unfired configuration and inner cartridge walls 23313 defining the longitudinal slot 23311. The inner cartridge walls 23313 each comprise a retention feature 23314 extending laterally inwardly into the longitudinal slot 23311 to prevent the sled 23330 from falling out of the bottom of the cartridge body 23310 and from moving out of the unfired position prior to being fired.

Figure 13:
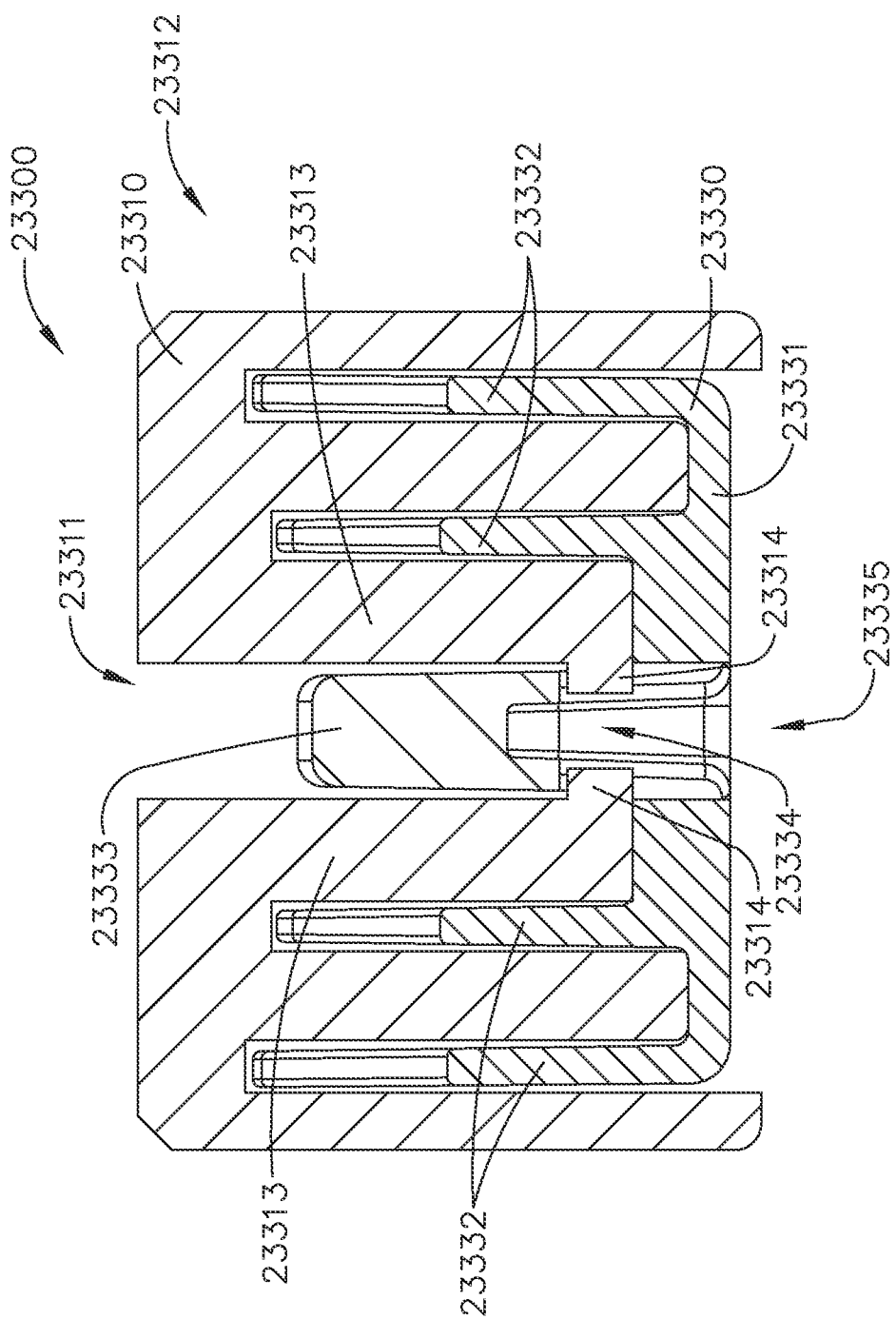
FIG. 13 is a cross-sectional view of the staple cartridge of FIG. 11 taken along line 13-13 in FIG. 12.
Figure 14:
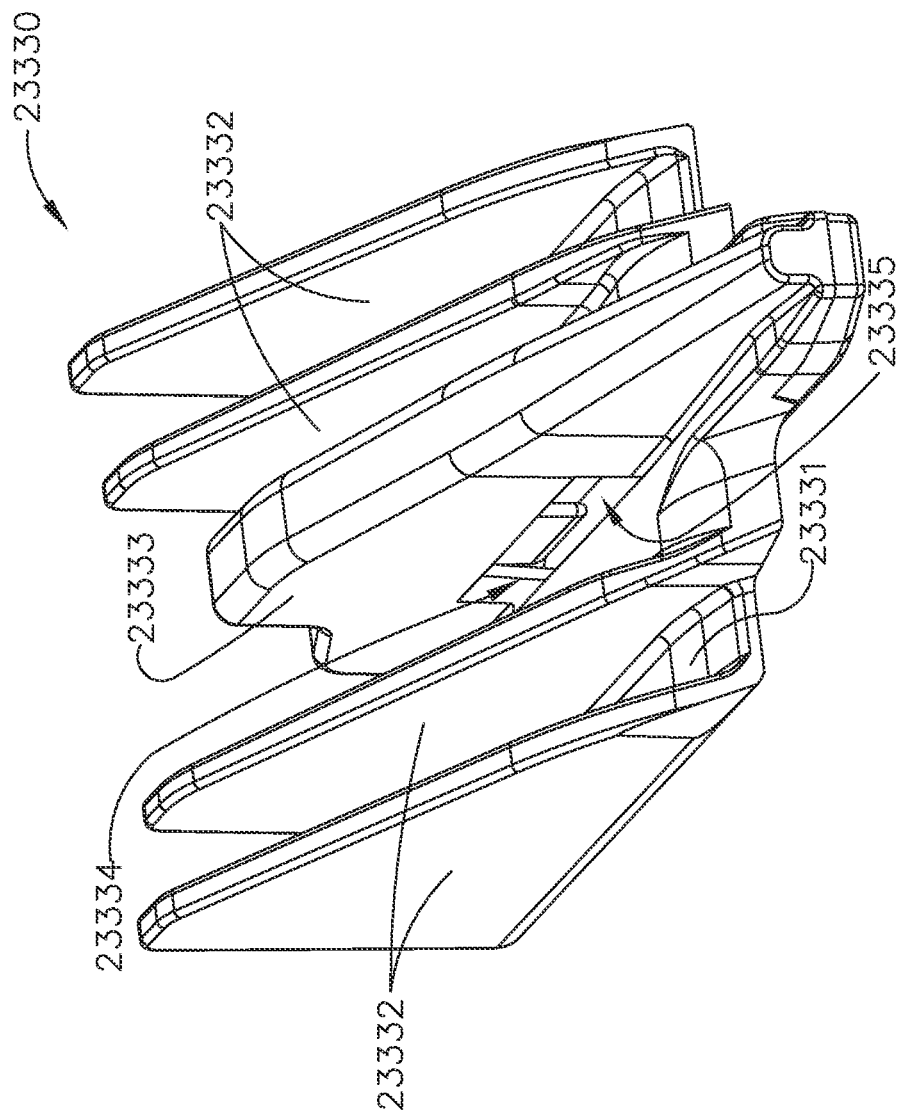
FIG. 14 is a perspective view of the sled of the staple cartridge of FIG. 11.

The sled 23330 comprises a bottom portion 23331 and ramped wedges 23332 extending upwardly from the bottom portion 23331 and into the cartridge body 23310. The ramped wedges 23332 are configured to lift the staple drivers 23320 to eject the staples supported thereon as the sled 23330 is moved distally through the cartridge body 23310 during the staple firing stroke. The sled 23330 further comprises a central portion 23333 that moves within the longitudinal slot 23311 of the cartridge body 23310 as the sled 23330 is moved distally. The cartridge body 23310 further comprises retention features, or shoulders, 23314 that extend inwardly toward the central portion 23333 of the sled 23330 that releasably hold the sled 23330 in its proximal unfired position. More specifically, the retention features 23314 extend into retention cavities 23334 defined in the central portion 23333 of the sled 23330 when the sled 23330 is in its unfired position. As can be seen in FIG. 13, the retention features 23314 comprise inwardly-extending ledges extending from the inner cartridge walls 23313. The retention features 23314 can be snap-fit, friction-fit, and/or press-fit into the retention cavities 23334, for example. When a firing driver of a surgical stapling assembly is advanced distally into contact with the sled 23330 at the beginning of the staple firing stroke, the firing driver pushes the sled 23330 distally out of engagement with the retention features 23334.

Figure 8:
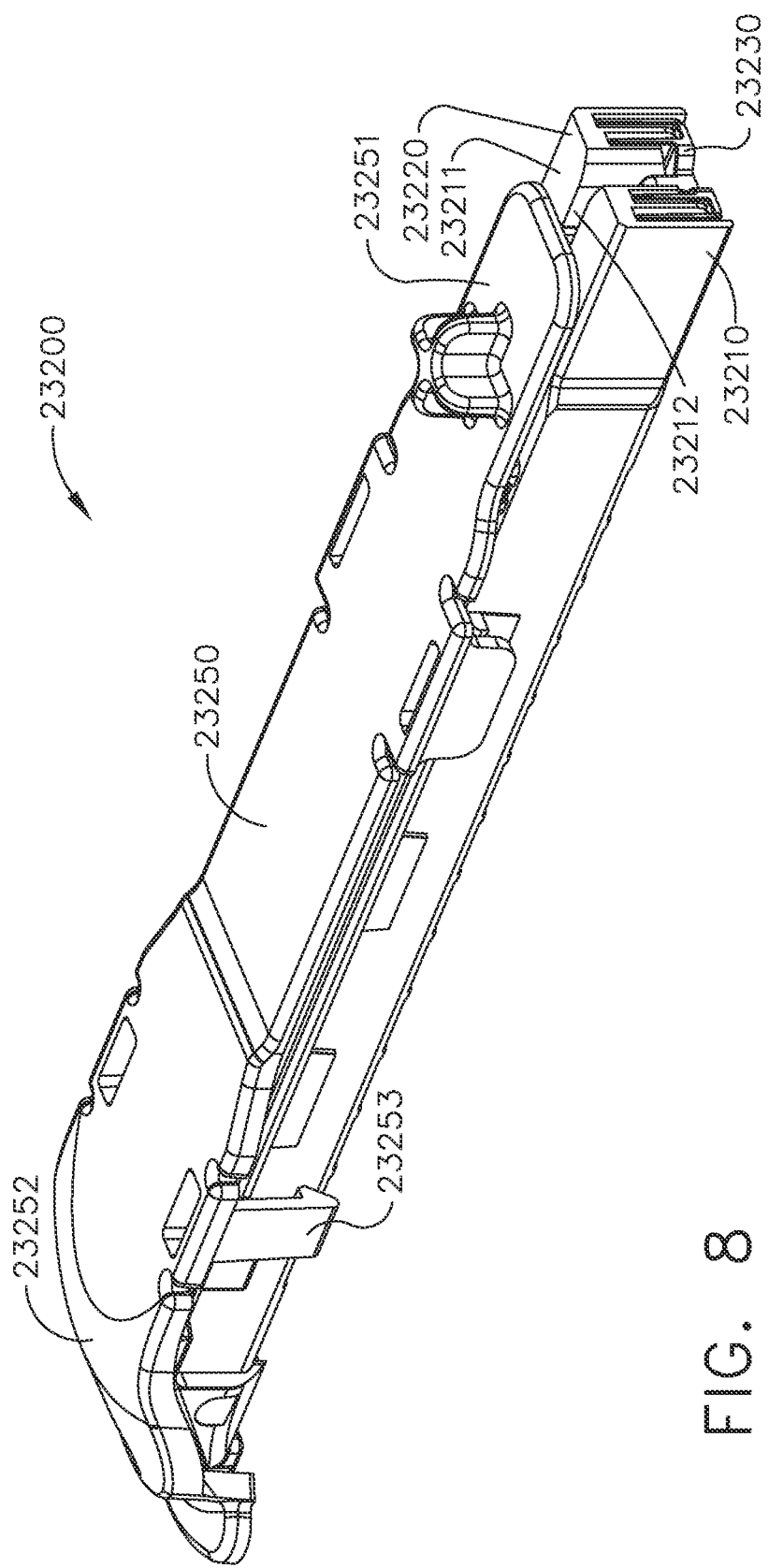
FIG. 8 is a perspective view of a staple cartridge in accordance with the present disclosure comprising a cartridge body, a sled, and a staple retainer configured to hold the sled in an unfired position prior to removal of the staple retainer from the cartridge body.

As discussed above, referring again to FIG. 8, a retainer can be removably attached to a cartridge body of a staple cartridge that, among other things, prevents a sled from being accidentally moved within the cartridge body while the staple cartridge is being shipped, handled, and/or installed in a stapling instrument. In the event that the sled is moved distally accidentally, the sled may inadvertently eject, or at least partially eject, some of the proximal-most staples stored in the staple cartridge. Moreover, the sled may unlock the staple firing drive of a stapling instrument when the staple cartridge is installed in the stapling instrument and the sled is in its proximal unfired position. If, however, the sled is not in its unfired position when the staple cartridge is installed in the stapling instrument, the sled may not unlock the firing drive and the stapling instrument may stay in a locked state until the staple cartridge is replaced. The entire disclosure of U.S. Pat. No. 6,988,649, entitled SURGICAL STAPLING INSTRUMENT HAVING A SPENT CARTRIDGE LOCKOUT, which issued on Jun. 24, 2006, is incorporated by reference herein.

In accordance with the present disclosure, the sled 23330 can be movable from a shipped position to an unfired, ready-to-fire position when a staple retainer is removed from the staple cartridge. The retention features 23314 of the cartridge body 23310 can engage with the sled 23330 when the sled 23330 is in the shipped position. When the staple retainer is lifted away from the cartridge body 23310, the staple retainer holds onto the sled 23330 and pulls the sled 23330 distally out of its shipped position into an unfired ready-to-fire position. In effect, the staple retainer pulls the sled 23330 out of engagement with the retention features 23314. The retention features 23314 can be configured to be broken by the staple retainer so as to place the sled 23330 in the ready to fire position. The act of breaking the retention features 23314 can reposition the sled 23330 from its shipped position to another relative longitudinal position where the sled 23330 is ready to be fired. In accordance with the present disclosure, the cartridge body 23310 may comprise a stop that is contacted by the sled 23330 when the sled 23330 is pulled distally which stops the distal movement of the sled 23330.

FIGS. 15 and 16 depict a surgical stapling assembly 23400 comprising a staple cartridge 23401 and a cartridge channel 23410 within which the staple cartridge 23401 is configured to be installed. The cartridge channel 23410 comprises a bottom portion 23411 and channel sidewalls 23412 extending upwardly from the bottom portion 23411. The staple cartridge 23401 comprises a cartridge body 23420, staple drivers, staples, and a sled 23440 movable through the cartridge body 23420 from an unfired position to a fired position during a staple firing stroke. The sled 23440 comprises a bottom portion 23441 and sled ramps 23442 extending upwardly into the cartridge body 23420 that are configured to lift the staple drivers during the staple firing stroke to eject the staples from the cartridge body 23420.

The cartridge body 23420 comprises a deck 23421 and a longitudinal slot 23422 configured to receive at least a portion of a firing driver therein during the staple firing stroke. The cartridge body 23420 comprises inner cartridge walls 23425 defining the longitudinal slot 23422, intermediate cartridge walls 23426, and outer cartridge walls 23427 that are positioned adjacent to and supported by the channel sidewalls 23412 when the staple cartridge 23401 is installed in the cartridge channel 23410. In accordance with the present disclosure, the staple cartridge 23401 may not comprise a pan to hold drivers, staples, and/or the sled 23440 in the cartridge body 23420 when the staple cartridge assembly 23401 is not installed in the cartridge channel 23410. The outer cartridge walls 23427 each comprise a ledge tab 23428 extending laterally inwardly toward the longitudinal slot 23422 configured to prevent the sled 23440 from falling out of the bottom of the cartridge body 23420. The cartridge channel 23410 comprises notches 23413 defined therein that are configured to receive the ledge tabs 23428 when the staple cartridge 23401 is seated in the cartridge channel 23410. The ledge tabs 23428 of the staple cartridge 23401 are closely received within the notches 23413 of the cartridge channel 23410 and are restrained from moving horizontally, longitudinally, and downwardly with respect to the cartridge channel 23410 which can prevent or at least limit relative movement between the staple cartridge 23401 and the cartridge channel 23410.

Various aspects of the subject matter described herein are set out in the following examples.

Example 1—A staple cartridge assembly (23050, 23100) for use with a surgical stapling instrument (23000), wherein the staple cartridge assembly comprises a plurality of staples (23001), a plurality of staple drivers (23090), a cartridge body (23051) comprising a proximal end (23055), a distal end (23056), a longitudinal axis extending between the proximal end and the distal end, a deck (23052) configured to support patient tissue, a longitudinal cartridge slot (23054) configured to receive at least a portion of a firing driver (23040) of the surgical stapling instrument during a firing stroke, a plurality of staple cavities (23053) defined in the deck, wherein the staples are removably stored within the staple cavities and a retention feature (23060). The staple cartridge assembly further comprises a sled (23080) movable longitudinally through the cartridge body from a proximal unfired position to a distal fired position during a firing stroke, wherein the sled comprises a ramp (23082, 23083) configured to lift the staple drivers toward the deck to eject the staples from the staple cavities during the firing stroke, wherein the sled comprises a longitudinally-extending slot (23085), wherein the retention feature supports at least one of the staple drivers in an unlifted position, and wherein the longitudinally-extending slot of the sled is configured to receive the retention feature during the firing stroke.

Example 2—The staple cartridge assembly of Example 1, wherein the longitudinally-extending slot is defined in the ramp.

Example 3—The staple cartridge assembly of Example 1, wherein the ramp comprises a first ramp, wherein the sled further comprises a second ramp, wherein the first ramp is positioned intermediate the longitudinal cartridge slot and the second ramp, wherein the longitudinally-extending slot is defined in the second ramp, and wherein the longitudinally-extending slot faces away from the longitudinal cartridge slot.

Example 4—The staple cartridge assembly of Examples 1, 2, or 3, wherein the cartridge body further comprises an outer cartridge wall (23059) defining a lateral side of the cartridge body, wherein the retention feature comprises a projection that extends inwardly from the outer cartridge wall toward the sled, and wherein the projection is positioned within the longitudinally-extending slot when the sled is advanced distally toward the distal fired position during the firing stroke.

Example 5—The staple cartridge assembly of Example 4, wherein the projection is integrally formed with the outer cartridge wall.

Example 6—The staple cartridge assembly of Examples 1, 2, or 3, wherein the cartridge body further comprises an outer cartridge wall (23059) defining a lateral side of the cartridge body, wherein the retention feature comprises a first projection and a second projection, wherein the first projection and the second projection extend inwardly from the outer cartridge wall toward the longitudinal cartridge slot, wherein the second projection is positioned distally with respect to the first projection, wherein the first projection is positioned within the longitudinally-extending slot of the sled when the sled is in the proximal unfired position, and wherein the second projection is positioned with the longitudinally-extending slot of the sled when the sled is advanced distally toward the distal fired position during the firing stroke.

Example 7—The staple cartridge assembly of Example 6, wherein the second projection is configured to releasably hold one of the staple drivers in an unlifted position.

Example 8—The staple cartridge assembly of Examples 6 or 7, wherein the first projection is configured to releasably hold one of the staple drivers in an unlifted position.

Example 9—The staple cartridge assembly of Examples 4, 5, 6, or 7, wherein the first projection and the second projection are integrally formed with the outer cartridge wall.

Example 10—The staple cartridge assembly of Examples 1, 2, or 3, wherein the cartridge body further comprises a bottom and an outer cartridge wall defining a lateral side of the cartridge body, wherein the retention feature comprises a plurality of projections arranged along a longitudinal projection axis, wherein each projection extends inwardly from the outer cartridge wall toward the longitudinal cartridge slot, and wherein the projections prevent the staple drivers from falling out of the bottom of the cartridge body.

Example 11—The staple cartridge assembly of Example 9, wherein the projections are integrally formed with the outer cartridge wall.

Example 12—The staple cartridge assembly of Examples 1, 2, or 3, wherein the cartridge body further comprises a longitudinal cartridge wall (23059), wherein the retention feature comprises a projection that extends inwardly from the longitudinal cartridge wall toward the sled, and wherein the projection is positioned within the longitudinally-extending slot when the sled is advanced distally toward the distal fired position during the firing stroke.

Example 13—The staple cartridge assembly of Examples 1, 2, 3, 4, 5, 6, 10, 11, or 12, wherein the retention feature releasably secures at least one of the staple drivers in an unlifted position.

Example 14—The staple cartridge assembly of Examples 1, 2, 3, 4, 5, 6, 7, 8, 9, 10, 11, 12, or 13, wherein the retention feature is formed with a thermal staking process.

Example 15—The staple cartridge assembly of Examples 1, 2, 3, 4, 5, 6, 7, 8, 9, 10, 11, 12, 13, or 14, wherein the retention feature is configured to releasably hold the sled in the proximal unfired position.

Example 16—A staple cartridge assembly for use with a surgical stapling instrument, wherein the staple cartridge assembly comprises a plurality of staples, a plurality of staple drivers, and a cartridge body comprising a proximal end, a distal end, a longitudinal axis extending between the proximal end and the distal end, a deck configured to support patient tissue, a longitudinal cartridge slot configured to receive at least a portion of a firing driver of the surgical stapling instrument during a firing stroke, a plurality of staple cavities defined in the deck, wherein the staples are removably stored within the staple cavities, and a retention feature. The staple cartridge assembly further comprises a sled movable longitudinally through the cartridge body from a proximal unfired position to a distal fired position during a firing stroke, wherein the sled comprises a ramp configured to lift the staple drivers toward the deck to eject the staples from the staple cavities during the firing stroke, wherein the sled comprises a longitudinally-extending slot, wherein the retention feature supports at least one of the staple drivers in an unlifted position, and wherein the longitudinally-extending slot of the sled is configured to receive the retention feature during the firing stroke.

Example 17—The staple cartridge assembly of Example 16, wherein the longitudinally-extending slot is defined in the ramp.

Example 18—The staple cartridge assembly of Examples 16 or 17, wherein the ramp comprises a first ramp, wherein the sled further comprises a second ramp, wherein the first ramp is positioned intermediate the longitudinal cartridge slot and the second ramp, wherein the longitudinally-extending slot is defined in the second ramp, and wherein the longitudinally-extending slot faces away from the longitudinal cartridge slot.

Example 19—The staple cartridge assembly of Examples 16, 17, or 18, wherein the cartridge body further comprises an outer cartridge wall defining a lateral side of the cartridge body, wherein the retention feature comprises a projection that extends inwardly from the outer cartridge wall toward the sled, and wherein the projection is positioned within the longitudinally-extending slot when the sled is advanced distally toward the distal fired position during the firing stroke.

Example 20—The staple cartridge assembly of Example 19, wherein the projection is integrally formed with the outer cartridge wall.

Example 21—The staple cartridge assembly of Examples 16, 17, 18, 19, or 20, wherein the cartridge body further comprises an outer cartridge wall defining a lateral side of the cartridge body, wherein the retention feature comprises a first projection and a second projection, wherein the first projection and the second projection extend inwardly from the outer cartridge wall toward the longitudinal cartridge slot, wherein the second projection is positioned distally with respect to the first projection, wherein the first projection is positioned within the longitudinally-extending slot of the sled when the sled is in the proximal unfired position, and wherein the second projection is positioned with the longitudinally-extending slot of the sled when the sled is advanced distally toward the distal fired position during the firing stroke.

Example 22—The staple cartridge assembly of Example 21, wherein the second projection is configured to releasably hold one of the staple drivers in an unlifted position.

Example 23—The staple cartridge assembly of Examples 21 or 22, wherein the first projection is configured to releasably hold one of the staple drivers in an unlifted position.

Example 24—The staple cartridge assembly of Examples 21, 22, or 23, wherein the first projection and the second projection are integrally formed with the outer cartridge wall.

Example 25—The staple cartridge assembly of Examples 16, 17, 18, 19, 20, 21, 22, 23, or 24, wherein the cartridge body further comprises a bottom and an outer cartridge wall defining a lateral side of the cartridge body, wherein the retention feature comprises a plurality of projections arranged along a longitudinal projection axis, wherein each projection extends inwardly from the outer cartridge wall toward the longitudinal cartridge slot, and wherein the projections prevent the staple drivers from falling out of the bottom of the cartridge body.

Example 26—The staple cartridge assembly of Example 25, wherein the projections are integrally formed with the outer cartridge wall.

Example 27—The staple cartridge assembly of Examples 16, 17, 18, 19, 20, 21, 22, 23, 24, 25, or 26, wherein the cartridge body further comprises a longitudinal cartridge wall, wherein the retention feature comprises a projection that extends inwardly from the longitudinal cartridge wall toward the sled, and wherein the projection is positioned within the longitudinally-extending slot when the sled is advanced distally toward the distal fired position during the firing stroke.

Example 28—The staple cartridge assembly of Examples 16, 17, 18, 19, 20, 21, 22, 23, 24, 25, 26, or 27, wherein the retention feature releasably secures at least one of the staple drivers in an unlifted position.

Example 29—The staple cartridge assembly of Examples 16, 17, 18, 19, 20, 21, 22, 23, 24, 25, 26, 27, or 28, wherein the retention feature is formed with a thermal staking process.

Example 30—The staple cartridge assembly of Examples 16, 17, 18, 19, 20, 21, 22, 23, 24, 25, 26, 27, 28, or 29, wherein the retention feature is configured to releasably hold the sled in the proximal unfired position.

Example 31—A staple cartridge assembly comprising a plurality of staples, a plurality of staple drivers, and a cartridge body comprising a proximal end, a distal end, a longitudinal axis extending between the proximal end and the distal end, a longitudinal cartridge slot configured to receive at least a portion of a firing driver of the surgical stapling instrument during a firing stroke, a plurality of staple cavities, wherein the staples are removably stored within the staple cavities, and an array of retention features positioned longitudinally along the cartridge body. The staple cartridge assembly further comprises a sled movable longitudinally through the cartridge body from a proximal unfired position to a distal fired position during a firing stroke, wherein the sled comprises a ramp configured to lift the staple drivers to eject the staples from the staple cavities during the firing stroke, wherein the sled comprises a longitudinally-extending slot, wherein the array of retention features supports the staple drivers in an unlifted position and the sled in the proximal unfired position, and wherein the array of retention features are further configured to vertically restrain the sled within the cartridge body during the firing stroke.

Example 32—The staple cartridge assembly of Example 31, wherein the array of retention features comprises a plurality of driver retention features (e.g., projections), wherein each driver retention feature extends inwardly from an outer lateral cartridge wall toward the longitudinal slot and into an outer staple cavity of an outer row of staple cavities.

Example 33—The staple cartridge assembly of Example 32, wherein the sled is configured to engage a proximal-most driver retention feature of the plurality of driver retention features prior to disengaging a proximal-most sled retention feature (e.g., projection) of the array of retention features.

Example 34—A staple cartridge assembly comprising a plurality of staples, a plurality of staple drivers, and a cartridge body comprising a proximal end, a distal end, a longitudinal axis extending between the proximal end and the distal end, a longitudinal cartridge slot configured to receive at least a portion of a firing driver of the surgical stapling instrument during a firing stroke, a plurality of staple cavities, wherein the staples are removably stored within the staple cavities, and a plurality of retention features. The staple cartridge assembly further comprises a sled movable longitudinally through the cartridge body from a proximal unfired position to a distal fired position during a firing stroke, wherein the plurality of retention features supports the staple drivers in an unlifted position, supports the sled in the proximal unfired position, and vertically restrain the sled within the cartridge body during the firing stroke, wherein the plurality of retention features comprises a first plurality of retention features proximal to the plurality of staple cavities and a second plurality of retention features distal to the first plurality of retention features.

Example 35—The staple cartridge assembly of Example 34, wherein the plurality of retention features are formed with a thermal staking process.

Many of the surgical instrument systems described herein are motivated by an electric motor; however, the surgical instrument systems described herein can be motivated in any suitable manner. In accordance with the present disclosure, the surgical instrument systems described herein can be motivated by a manually-operated trigger, for example. The motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail.

The surgical instrument systems described herein have been described in connection with the deployment and deformation of staples; however, the present disclosure may not be so limited. The present disclosure envisions that fasteners other than staples can be deployed, such as clamps or tacks, for example. Moreover, the present disclosure envisions utilizing any suitable means for sealing tissue. An end effector in accordance with the present disclosure can comprise electrodes configured to heat and seal the tissue. Also, an end effector in accordance with the present disclosure can apply vibrational energy to seal the tissue.

The entire disclosures of U.S. Pat. No. 10,213,203, entitled STAPLE CARTRIDGE ASSEMBLY WITHOUT A BOTTOM COVER, which issued on Feb. 26, 2019, U.S. Pat. No. 10,945,727, entitled STAPLE CARTRIDGE WITH DEFORMABLE DRIVER RETENTION FEATURES, which issued on Mar. 16, 2021, U.S. Pat. No. 11,234,698, entitled STAPLING SYSTEM COMPRISING A CLAMP LOCKOUT AND A FIRING LOCKOUT, which issued on Feb. 1, 2022, U.S. Pat. No. 11,540,826, entitled SURGICAL STAPLER END EFFECTOR SLED HAVING CARTRIDGE WALL SUPPORT FEATURE, which issued on Jan. 3, 2023, U.S. Pat. No. 10,299,792, entitled FASTENER CARTRIDGE COMPRISING NON-UNIFORM FASTENERS, which issued on May 28, 2019, U.S. Pat. No. 8,540,133, entitled STAPLE CARTRIDGE, which issued on Sep. 24, 2013, U.S. Pat. No. 9,788,835, entitled DEVICES AND METHODS FOR FACILITATING EJECTION OF SURGICAL FASTENERS FROM CARTRIDGES, which issued on Oct. 17, 2017, U.S. Pat. No. 10,105,142, entitled SURGICAL STAPLER WITH PLURALITY OF CUTTING ELEMENTS, which issued on Oct. 23, 2018, U.S. Pat. No. 10,537,324, entitled STEPPED STAPLE CARTRIDGE WITH ASYMMETRICAL STAPLES, which issued on Jan. 21, 2020, U.S. Pat. No. 7,669,746, entitled STAPLE CARTRIDGES FOR FORMING STAPLES HAVING DIFFERING FORMED STAPLE HEIGHTS, which issued on Mar. 2, 2010, U.S. Pat. No. 8,123,100, entitled SURGICAL STAPLING INSTRUMENTS INCLUDING A CARTRIDGE HAVING MULTIPLE STAPLE SIZES, which issued on Feb. 28, 2012, U.S. Pat. No. 7,407,075, entitled STAPLE CARTRIDGE HAVING MULTIPLE STAPLE SIZES FOR A SURGICAL STAPLING INSTRUMENT, which issued on Aug. 5, 2008, U.S. Pat. No. 10,085,749, entitled SURGICAL APPARATUS WITH CONDUCTOR STRAIN RELIEF, which issued on Oct. 2, 2018, U.S. Pat. No. 10,765,427, entitled METHOD FOR ARTICULATING A SURGICAL INSTRUMENT, which issued on Sep. 8, 2020, U.S. Pat. No. 11,291,445, entitled SURGICAL STAPLE CARTRIDGES WITH INTEGRAL AUTHENTICATION KEYS, which issued on Apr. 5, 2022, U.S. Pat. No. 8,864,007, entitled IMPLANTABLE FASTENER CAR- TRIDGE HAVING A NON-UNIFORM ARRANGEMENT, which issued on Oct. 21, 2014, U.S. Pat. No. 11,490,890, entitled COMPRESSIBLE NON-FIBROUS ADJUNCTS, which issued on Nov. 8, 2022, U.S. Pat. No. 10,952,724, entitled THREE DIMENSIONAL ADJUNCTS, which issued on Mar. 23, 2021, U.S. Pat. No. 9,770,245, entitled LAYER ARRANGEMENTS FOR SURGICAL STAPLE CARTRIDGES, which issued on Sep. 26, 2017, U.S. Pat. No. 10,123,798, entitled TISSUE THICKNESS COMPENSATOR COMPRISING CONTROLLED RELEASE AND EXPANSION, which issued on Nov. 13, 2018, U.S. Pat. No. 10,166,023, entitled METHOD OF APPLYING A BUTTRESS TO A SURGICAL STAPLER END EFFECTOR, which issued on Jan. 1, 2019, U.S. Pat. No. 11,207,065, entitled METHOD FOR FABRICATING SURGICAL STAPLER ANVILS, which issued on Dec. 28, 2021, U.S. Pat. No. 8,141,762, entitled SURGICAL STAPLER COMPRISING A STAPLE POCKET, which issued on Mar. 27, 2012, U.S. Pat. No. 8,876,857, entitled END EFFECTOR WITH REDUNDANT CLOSING MECHANISMS, which issued on Nov. 4, 2014, U.S. Pat. No. 9,629,631, entitled COMPOSITE DRIVE BEAM FOR SURGICAL STAPLING, which issued on Apr. 25, 2017, U.S. Patent Application Publication No. 2022/0346858, entitled METHOD FOR OPERATING A SURGICAL INSTRUMENT INCLUDING SEGMENTED ELECTRODES, which published on Nov. 3, 2022, U.S. Patent Application Publication No. 2022/0304680, entitled DRIVERS FOR FASTENER CARTRIDGE ASSEMBLIES HAVING ROTARY DRIVE SCREWS, which published on Sep. 29, 2022, U.S. Patent Application Publication No. 2022/0304679, entitled METHOD OF USING A POWERED STAPLING DEVICE, which published on Sep. 29, 2022, U.S. Patent Publication No. 2019/0298350, entitled METHODS FOR CONTROLLING A POWERED SURGICAL STAPLER THAT HAS SEPARATE ROTARY CLOSURE AND FIRING SYSTEMS, which published on Oct. 3, 2019, U.S. Patent Application Publication No. 2017/0367695, entitled STAPLE CARTRIDGE COMPRISING WIRE STAPLES AND STAMPED STAPLES, which published on Dec. 28, 2017, U.S. Patent Application Publication No. 2015/0134077, entitled SEALING MATERIALS FOR USE IN SURGICAL STAPLING, which published on May 14, 2015, U.S. Patent Application Publication No. 2018/0168615, entitled METHOD OF DEFORMING STAPLES FROM TWO DIFFERENT TYPES OF STAPLE CARTRIDGES WITH THE SAME SURGICAL STAPLING INSTRUMENT, which published on Jun. 21, 2018, U.S. Patent Application Publication No. 2018/0132849, entitled STAPLE FORMING POCKET CONFIGURATIONS FOR CIRCULAR SURGICAL STAPLER ANVIL, which published on May 17, 2018, U.S. Patent Application Publication No. 2018/0168613, entitled SURGICAL INSTRUMENTS WITH JAWS THAT ARE PIVOTABLE ABOUT A FIXED AXIS AND INCLUDE SEPARATE AND DISTINCT CLOSURE AND FIRING SYSTEMS, which published on Jun. 21, 2018, U.S. Patent Application Publication No. 2017/0319205, entitled POWERED END EFFECTOR ASSEMBLY WITH PIVOTABLE CHANNEL, which published on Nov. 9, 2017, U.S. Patent Application Publication No. 2014/0001231, entitled FIRING SYSTEM LOCKOUT ARRANGEMENTS FOR SURGICAL INSTRUMENTS, which published on Jan. 2, 2014, U.S. Patent Application Publication No. 2016/0095596, entitled APPARATUS FOR ENDOSCOPIC PROCEDURES, which published on Apr. 7, 2016, U.S. Patent Application Publication No. 2015/0297199, entitled ADAPTER ASSEMBLY WITH GIMBAL FOR INTERCONNECTING ELECTROMECHANICAL SURGICAL DEVICES AND SURGICAL LOADING UNITS, AND SURGICAL SYSTEMS THEREOF, which published on Oct. 22, 2015, U.S. Patent Application Publication No. 2022/0031351, entitled SURGICAL INSTRUMENTS WITH DIFFERENT ARTICULATION JOINT ARRANGEMENTS FOR ACCOMMODATING FLEXIBLE ACTUATORS, which published on Feb. 3, 2022, U.S. Patent Application Publication No. 2022/0031320, entitled SURGICAL INSTRUMENTS WITH FLEXIBLE FIRING MEMBER ACTUATOR CONSTRAINT ARRANGEMENTS, which published on Feb. 3, 2022, U.S. Patent Application Publication No. 2023/0119119, entitled CABLE-DRIVEN ACTUATION SYSTEM FOR ROBOTIC SURGICAL TOOL ATTACHMENT, which published on Apr. 20, 2023, International Patent Publication No. WO2018/071497, entitled STAPLER CARTRIDGE WITH AN INTEGRAL KNIFE, which published on Apr. 18, 2018, International Patent Publication No. WO2018/049211, entitled WRIST ARCHITECTURE, which published on Mar. 15, 2018, U.S. Design Pat. No. D974,560, entitled STAPLE CARTRIDGE, which issued on Jan. 3, 2023, U.S. Design Pat. No. D967,421, entitled STAPLE CARTRIDGE, which issued on Oct. 18, 2022, and U.S. Design Patent No. D933,220, entitled BUTTRESS ASSEMBLY FOR A SURGICAL STAPLER, which issued on Oct. 12, 2021 are incorporated by reference herein.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/235,972, entitled MOTORIZED SURGICAL INSTRUMENT, now U.S. Pat. No. 9,050,083.

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one or more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

It is worthy to note that any reference numbers included in the appended claims are used to reference exemplary embodiments/elements described in the present disclosure. Accordingly, any such reference numbers are not meant to limit the scope of the subject matter recited in the appended claims.

While this invention has been described as having exemplary designs, the present invention may be further modified within the spirit and scope of the disclosure. This application is therefore intended to cover any variations, uses, or adaptations of the invention using its general principles.

It is worthy to note that any reference numbers included in the appended claims are used to reference exemplary embodiments/elements described in the present disclosure. Accordingly, any such reference numbers are not meant to limit the scope of the subject matter recited in the appended claims.

What is claimed is:

1. A staple cartridge assembly for use with a surgical stapling instrument, wherein the staple cartridge assembly comprises:
    a plurality of staples;
    a plurality of staple drivers;
    a cartridge body, comprising:
        a proximal end;
        a distal end;
        a longitudinal axis extending between the proximal end and the distal end;
        a deck configured to support patient tissue;
        a longitudinal cartridge slot configured to receive at least a portion of a firing driver of the surgical stapling instrument during a firing stroke;
        a plurality of staple cavities defined in the deck, wherein the staples are removably stored within the staple cavities; and
        a projection extending inwardly towards the longitudinal cartridge slot; and
    a sled movable longitudinally through the cartridge body from a proximal unfired position to a distal fired position during a firing stroke, wherein the sled comprises a ramp configured to lift the staple drivers toward the deck to eject the staples from the staple cavities during the firing stroke, wherein the sled comprises a longitudinally-extending slot, wherein the projection engagingly supports at least one of the staple drivers in an unlifted position, and wherein the longitudinally-extending slot of the sled is configured to receive the projection during the firing stroke.

2. The staple cartridge assembly of claim 1, wherein the longitudinally-extending slot is defined in the ramp.

3. The staple cartridge assembly of claim 1, wherein the ramp comprises a first ramp, wherein the sled further comprises a second ramp, wherein the first ramp is positioned intermediate the longitudinal cartridge slot and the second ramp, wherein the longitudinally-extending slot is defined in the second ramp, and wherein the longitudinally-extending slot faces away from the longitudinal cartridge slot.

4. The staple cartridge assembly of claim 1, wherein the cartridge body further comprises a first outer cartridge wall defining a first lateral side of the cartridge body and a second outer cartridge wall defining second lateral side of the cartridge body opposite the first lateral side of the cartridge body, wherein the projection extends inwardly from the first outer cartridge wall toward the sled, and wherein the projection is positioned within and slides along the longitudinally-extending slot during a portion of the firing stroke when the sled is advanced distally toward the distal fired position.

5. The staple cartridge assembly of claim 4, wherein the projection is integrally formed with the first outer cartridge wall.

6. The staple cartridge assembly of claim 1, wherein the cartridge body further comprises an outer cartridge wall defining a lateral side of the cartridge body, wherein the projection comprises a first projection and a second projection, wherein the first projection and the second projection extend inwardly from the outer cartridge wall toward the longitudinal cartridge slot, wherein the second projection is positioned distally with respect to the first projection, wherein the first projection is positioned within the longitudinally-extending slot of the sled when the sled is in the proximal unfired position, and wherein the second projection is positioned within the longitudinally-extending slot of the sled when the sled is advanced distally toward the distal fired position during the firing stroke.

7. The staple cartridge assembly of claim 6, wherein the second projection is configured to releasably hold one of the staple drivers in an unlifted position.

8. The staple cartridge assembly of claim 6, wherein the first projection is configured to releasably hold one of the staple drivers in an unlifted position.

9. The staple cartridge assembly of claim 6, wherein the first projection and the second projection are integrally formed with the outer cartridge wall.

10. The staple cartridge assembly of claim 1, wherein the cartridge body further comprises:
a pan-less bottom; and
an outer cartridge wall defining a lateral side of the cartridge body, wherein the projection comprises a plurality of projections arranged along a longitudinal projection axis, wherein each projection extends inwardly from the outer cartridge wall toward the longitudinal cartridge slot, and wherein the projections prevent the staple drivers from falling out of the pan-less bottom of the cartridge body.

11. The staple cartridge assembly of claim 10, wherein the projections are integrally formed with the outer cartridge wall.

12. The staple cartridge assembly of claim 1, wherein the cartridge body further comprises a longitudinal cartridge wall, wherein the projection extends inwardly from the longitudinal cartridge wall toward the sled, and wherein the projection is positioned within the longitudinally-extending slot when the sled is advanced distally toward the distal fired position during the firing stroke.

13. The staple cartridge assembly of claim 1, wherein the projection releasably secures at least one of the staple drivers in an unlifted position.

14. The staple cartridge assembly of claim 1, wherein the projection is formed with a thermal staking process.

15. The staple cartridge assembly of claim 1, wherein the projection comprises a plurality of projections, wherein a first projection of the plurality of projections is configured to releasably hold the sled in the proximal unfired position.

16. A staple cartridge assembly, comprising:
a plurality of staples;
a plurality of staple drivers;
a cartridge body, comprising:
a proximal end;
a distal end;
a longitudinal axis extending between the proximal end and the distal end;
a longitudinal cartridge slot configured to receive at least a portion of a firing driver of a surgical stapling instrument during a firing stroke;
a plurality of staple cavities, wherein the staples are removably stored within the staple cavities; and
an array of projections extending inwardly towards the longitudinal cartridge slot and positioned longitudinally along the cartridge body; and
a sled movable longitudinally through the cartridge body from a proximal unfired position to a distal fired position during a firing stroke, wherein the sled comprises a ramp configured to lift the staple drivers to eject the staples from the staple cavities during the firing stroke, wherein the sled comprises a longitudinally-extending slot, wherein the array of projections supports the staple drivers in an unlifted position and the sled in the proximal unfired position, and wherein the array of projections is configured to extend into the longitudinally-extending slot of the sled to vertically restrain the sled within the cartridge body during the firing stroke.

17. The staple cartridge assembly of claim 16, wherein the array of projections comprises a plurality of driver retention projections, wherein each driver retention projection extends inwardly from an outer lateral cartridge wall toward the longitudinal cartridge slot and into an outer staple cavity of an outer row of staple cavities.

18. The staple cartridge assembly of claim 17, wherein a proximal-most projection of the array of projections comprises a sled-retention projection, wherein a proximal-most driver retention projection of the plurality of driver retention projections is positioned distally with respect to the proximal-most sled retention projection, and wherein the sled is configured to engage the proximal-most driver retention projection prior to disengaging the proximal-most sled retention projection during the firing stroke.

19. A staple cartridge assembly, comprising:
a plurality of staples;
a plurality of staple drivers;
a cartridge body, comprising:
a proximal end;
a distal end;

a longitudinal axis extending between the proximal end and the distal end;

a longitudinal cartridge slot configured to receive at least a portion of a firing driver of a surgical stapling instrument during a firing stroke;

a plurality of staple cavities, wherein the staples are removably stored within the staple cavities; and a plurality of projections extending inwardly towards the longitudinal cartridge slot;

a sled movable longitudinally through the cartridge body from a proximal unfired position to a distal fired position during a firing stroke, wherein the sled comprises a longitudinally-extending notch, wherein the plurality of projections supports the staple drivers in an unlifted position, supports the sled in the proximal unfired position, and vertically restrains the sled within the cartridge body during the firing stroke, wherein the plurality of projections comprises:

a first plurality of projections proximal to the plurality of staple cavities; and a second plurality of projections distal to the first plurality of projections, wherein each of the second plurality of projections supports a staple driver of the plurality of staple drivers in the unlifted position and extends into the longitudinally-extending notch to vertically restrain the sled during at least a portion of the firing stroke.

20. The staple cartridge assembly of claim 19, wherein the cartridge body comprises a pan-less bottom, and wherein each of the plurality of projections are formed with a thermal staking process.

* * * * *